(12) United States Patent
Metzger et al.

(10) Patent No.: US 11,771,442 B2
(45) Date of Patent: *Oct. 3, 2023

(54) BI-CRUCIATE KNEE SYSTEM

(71) Applicant: Biomet Manufacturing Corp., Warsaw, IN (US)

(72) Inventors: Robert Metzger, Wakarusa, IN (US); Adolph V. Lombardi, New Albany, OH (US); Christopher Peters, Murray, UT (US); Jeffrey DeClaire, Rochester Hills, MI (US); Keith Berend, Columbus, OH (US); Craig Della Valle, Chicago, IL (US); Brad Durcholz, Warsaw, IN (US); Brice Bedke, North Manchester, IN (US)

(73) Assignee: Biomet Manufacturing LLC, Warsaw, IN (US)

( * ) Notice: Subject to any disclaimer, the term of this patent is extended or adjusted under 35 U.S.C. 154(b) by 966 days.

This patent is subject to a terminal disclaimer.

(21) Appl. No.: 16/419,459

(22) Filed: May 22, 2019

(65) Prior Publication Data
US 2019/0269422 A1 Sep. 5, 2019

Related U.S. Application Data

(63) Continuation of application No. 14/639,522, filed on Mar. 5, 2015, now abandoned, which is a
(Continued)

(51) Int. Cl.
*A61F 2/46* (2006.01)
*A61B 17/15* (2006.01)
(Continued)

(52) U.S. Cl.
CPC ........ *A61B 17/1764* (2013.01); *A61B 17/157* (2013.01); *A61F 2/461* (2013.01);
(Continued)

(58) Field of Classification Search
CPC .............. A61B 17/1764; A61B 17/157; A61B 17/1675; A61B 17/154; A61B 17/155;
(Continued)

(56) References Cited

U.S. PATENT DOCUMENTS

D274,094 S 5/1984 Kenna
4,759,350 A * 7/1988 Dunn .................... A61B 17/154
606/82

(Continued)

FOREIGN PATENT DOCUMENTS

CN 102149337 A 8/2011
CN 107530172 A 1/2018
(Continued)

OTHER PUBLICATIONS

"U.S. Appl. No. 13/470,630, 312 Amendment filed Sep. 10, 2015", 3 pgs.
(Continued)

*Primary Examiner* — Marcela I. Shirsat
(74) *Attorney, Agent, or Firm* — SCHWEGMAN LUNDBERG & WOESSNER, P.A.

(57) ABSTRACT

An instrumentation set for preparing a proximal tibia during a bi-cruciate retaining procedure can include a tibial resection block and a stylus. The tibial resection block can be configured to be fixed to an anterior portion of the proximal tibia. The tibial resection block can define a slot that extends in a medial-lateral direction when the tibial resection block is fixed to the proximal tibia. The stylus can have a first block attachment feature and a second block attachment feature. The first block attachment feature can be offset from the stylus a first distance. The second block attachment feature can be offset from the stylus a second distance. The first and second block attachment features of the stylus can be selectively and alternatively received by the slot of the
(Continued)

tibial resection block to position the stylus at distinct offset locations relative to the slot.

21 Claims, 28 Drawing Sheets

Related U.S. Application Data continuation-in-part of application No. 14/013,859, filed on Aug. 29, 2013, now abandoned, which is a continuation-in-part of application No. 13/470,630, filed on May 14, 2012, now Pat. No. 9,161,761.

(60) Provisional application No. 61/950,383, filed on Mar. 10, 2014, provisional application No. 61/593,521, filed on Feb. 1, 2012, provisional application No. 61/486,023, filed on May 13, 2011.

(51) Int. Cl.
*A61F 2/38* (2006.01)
*A61F 2/30* (2006.01)
*A61B 17/17* (2006.01)

(52) U.S. Cl.
CPC .......... *A61F 2/4637* (2013.01); *A61F 2/4657* (2013.01); *A61F 2/4684* (2013.01); *A61F 2/389* (2013.01); *A61F 2/3859* (2013.01); *A61F 2002/30688* (2013.01); *A61F 2002/30878* (2013.01); *A61F 2002/4631* (2013.01); *A61F 2002/4658* (2013.01); *A61F 2002/4668* (2013.01); *A61F 2002/4681* (2013.01)

(58) Field of Classification Search
CPC .. A61B 2090/061; A61F 2/461; A61F 2/4637; A61F 2/4657; A61F 2/389; A61F 2/4684; A61F 2002/4631; A61F 2002/4658; A61F 2002/4661; A61F 2002/4668; A61F 2002/4681; A61F 2002/30688; A61F 2002/30878; A61F 2/3859
USPC .... 606/88, 86 R–90, 96–98, 105, 54–59, 82; 600/214, 218–222
See application file for complete search history.

(56) References Cited

U.S. PATENT DOCUMENTS

| | | | |
|---|---|---|---|
| 4,769,040 A | 9/1988 | Wevers | |
| D326,156 S | 5/1992 | Martinez | |
| 5,137,536 A | 8/1992 | Koshino | |
| D346,218 S | 4/1994 | White | |
| D346,979 S | 5/1994 | Stalcup et al. | |
| 5,370,701 A | 12/1994 | Finn | |
| D358,211 S | 5/1995 | Cohen | |
| D358,647 S | 5/1995 | Cohen et al. | |
| D369,863 S | 5/1996 | Hayes | |
| D373,825 S | 9/1996 | Hayes | |
| 5,681,316 A | 10/1997 | DeOrio et al. | |
| 5,683,396 A | 11/1997 | Tokish et al. | |
| 5,702,464 A * | 12/1997 | Lackey ................. | A61F 2/4684 623/20.32 |
| 5,735,904 A | 4/1998 | Pappas | |
| 5,776,201 A | 7/1998 | Colleran et al. | |
| 6,047,826 A | 4/2000 | Kalinski et al. | |
| 6,126,692 A | 10/2000 | Robie et al. | |
| 6,485,519 B2 | 11/2002 | Meyers et al. | |
| 7,335,206 B2 | 2/2008 | Steffensmeier et al. | |
| 7,569,060 B2 | 8/2009 | Faoro | |
| 7,678,115 B2 | 3/2010 | D'alessio, II et al. | |
| D626,234 S | 10/2010 | Otto et al. | |
| 8,343,227 B2 | 1/2013 | Metzger et al. | |
| D685,909 S | 7/2013 | Lomicka et al. | |
| 8,715,359 B2 | 5/2014 | Deffenbaugh et al. | |
| 8,728,167 B2 | 5/2014 | Collazo | |
| 8,911,501 B2 | 12/2014 | Irwin et al. | |
| D729,189 S | 5/2015 | Kangasmaa et al. | |
| 9,161,761 B2 | 10/2015 | Metzger et al. | |
| 9,492,183 B2 * | 11/2016 | Wilkinson ........... | A61B 17/157 |
| 10,485,555 B2 * | 11/2019 | Metzger ................ | A61F 2/4657 |
| 2003/0130665 A1 * | 7/2003 | Pinczewski .......... | A61B 17/154 606/88 |
| 2004/0138755 A1 | 7/2004 | O'connor et al. | |
| 2004/0153162 A1 | 8/2004 | Sanford et al. | |
| 2004/0167531 A1 | 8/2004 | Hodorek | |
| 2004/0193280 A1 | 9/2004 | Webster et al. | |
| 2005/0149042 A1 | 7/2005 | Metzger | |
| 2006/0184176 A1 | 8/2006 | Straszheim-Morley et al. | |
| 2007/0173858 A1 * | 7/2007 | Engh ..................... | A61F 2/3859 606/99 |
| 2008/0091273 A1 | 4/2008 | Hazebrouck | |
| 2008/0215059 A1 | 9/2008 | Carignan et al. | |
| 2009/0125114 A1 * | 5/2009 | May ..................... | A61F 2/30721 623/20.14 |
| 2009/0222014 A1 | 9/2009 | Bojarski et al. | |
| 2010/0016980 A1 | 1/2010 | Donno et al. | |
| 2010/0030571 A1 | 2/2010 | Jones et al. | |
| 2010/0130665 A1 | 5/2010 | Beigbeder et al. | |
| 2010/0298947 A1 | 11/2010 | Unger | |
| 2010/0305575 A1 * | 12/2010 | Wilkinson ........... | A61B 17/157 606/88 |
| 2010/0305711 A1 * | 12/2010 | McKinnon ......... | A61B 17/1764 606/82 |
| 2010/0331848 A1 | 12/2010 | Smith et al. | |
| 2011/0040387 A1 | 2/2011 | Ries et al. | |
| 2011/0190898 A1 | 8/2011 | Lenz et al. | |
| 2012/0158152 A1 * | 6/2012 | Claypool ................ | A61F 2/389 623/20.32 |
| 2012/0179266 A1 | 7/2012 | Collazo | |
| 2012/0316563 A1 | 12/2012 | Metzger et al. | |
| 2012/0330429 A1 | 12/2012 | Axelson, Jr. et al. | |
| 2013/0325019 A1 * | 12/2013 | Thomas ............. | A61B 17/1764 606/88 |
| 2014/0066934 A1 | 3/2014 | Deirmengian et al. | |
| 2014/0207196 A1 | 7/2014 | Slagle et al. | |
| 2014/0243990 A1 | 8/2014 | Collazo et al. | |
| 2014/0296859 A1 | 10/2014 | Claypool et al. | |
| 2015/0173781 A1 | 6/2015 | Metzger et al. | |
| 2016/0045205 A1 | 2/2016 | Metzger et al. | |

FOREIGN PATENT DOCUMENTS

| | | | |
|---|---|---|---|
| JP | 2010504766 A | 2/2010 | |
| JP | 2012501774 A | 1/2012 | |
| JP | 2014521382 A | 8/2014 | |
| JP | 2018507074 A | 3/2018 | |
| WO | WO-9729696 A1 | 8/1997 | |
| WO | WO-2008091358 A1 * | 7/2008 | ......... A61B 17/1764 |
| WO | WO-2008091358 A1 | 7/2008 | |
| WO | WO-2010029333 A1 | 3/2010 | |
| WO | WO-2010138832 A1 | 12/2010 | |
| WO | WO-2012158604 A1 | 11/2012 | |
| WO | WO-2013063386 A1 | 5/2013 | |
| WO | WO-2016141274 A1 | 9/2016 | |

OTHER PUBLICATIONS

"U.S. Appl. No. 13/470,630, Final Office Action dated Jul. 3, 2014", 14 pgs.
"U.S. Appl. No. 13/470,630, Non Final Action with Restriction Requirement dated Oct. 9, 2013", 7 pgs.
"U.S. Appl. No. 13/470,630, Non Final Office Action dated Nov. 21, 2013", 11 pgs.
"U.S. Appl. No. 13/470,630, Non Final Office Action dated Dec. 18, 2014", 15 pgs.
"U.S. Appl. No. 13/470,630, Notice of Allowance dated Jun. 25, 2015", 9 pgs.
"U.S. Appl. No. 13/470,630, PTO Response to Rule 312 Communication dated Sep. 14, 2015", 2 pgs.

(56) References Cited

OTHER PUBLICATIONS

"U.S. Appl. No. 13/470,630, Response filed Feb. 21, 2014 to Non Final Office Action dated Nov. 21, 2013", 12 pgs.
"U.S. Appl. No. 13/470,630, Response filed Mar. 16, 2015 to Non Final Office Action dated Dec. 18, 2014", 16 pgs.
"U.S. Appl. No. 13/470,630, Response filed Sep. 29, 2014 to Final Office Action dated Jul. 3, 2014", 14 pgs.
"U.S. Appl. No. 13/470,630, Response filed Nov. 8, 2013 to Non Final Action with Restriction Requirement dated Oct. 9, 2013", 2 pgs.
"U.S. Appl. No. 13/470,630, Supplemental Response filed Mar. 17, 2015 to Non Final Office Action dated Dec. 18, 2014", 16 pgs.
"U.S. Appl. No. 14/013,859 Response filed Feb. 9, 2017 to Non Final Office Action dated Nov. 23, 2016", 10 pgs.
"U.S. Appl. No. 14/013,859, Final Office Action dated May 22, 2017", 11 pgs.
"U.S. Appl. No. 14/013,859, Non Final Office Action dated Sep. 21, 2017", 15 pgs.
"U.S. Appl. No. 14/013,859, Non Final Office Action dated Nov. 23, 2016", 11 pgs.
"U.S. Appl. No. 14/013,859, Response filed Aug. 21, 2017 to Final Office Action dated May 22, 2017", 12 pgs.
"U.S. Appl. No. 14/013,859, Response filed Jan. 9, 2018 to Non Final Office Action dated Sep. 21, 2017", 12 pgs.
"U.S. Appl. No. 14/013,859, Response filed Oct. 5, 2016 to Restriction Requirement dated Aug. 25, 2016", 8 pgs.
"U.S. Appl. No. 14/013,859, Restriction Requirement dated Aug. 25, 2016", 7 pgs.
"U.S. Appl. No. 14/639,522, Advisory Action dated Dec. 21, 2018", 3 pgs.
"U.S. Appl. No. 14/639,522, Final Office Action dated Sep. 27, 2018", 21 pgs.
"U.S. Appl. No. 14/639,522, Non Final Office Action dated Mar. 7, 2018", 21 pgs.
"U.S. Appl. No. 14/639,522, Response filed Jan. 14, 2019 to Advisory Action dated Dec. 21, 2018", 12 pgs.
"U.S. Appl. No. 14/639,522, Response filed Jun. 6, 2018 to Non Final Office Action dated Mar. 7, 2018", 15 pgs.
"U.S. Appl. No. 14/639,522, Response filed Nov. 21, 2018 to Final Office action dated Sep. 27, 2018", 16 pgs.
"U.S. Appl. No. 14/639,522, Response filed Dec. 4, 2017 to Restriction Requirement dated Oct. 5, 2017", 8 pgs.
"U.S. Appl. No. 14/639,522, Restriction Requirement dated Oct. 5, 2017", 8 pgs.
"U.S. Appl. No. 14/876,142, Final Office Action dated Apr. 11, 2019", 17 pgs.
"U.S. Appl. No. 14/876,142, Non Final Office Action dated Sep. 28, 2018", 18 pgs.
"U.S. Appl. No. 14/876,142, Preliminary Amendment filed Oct. 9, 2015", 7 pgs.
"U.S. Appl. No. 14/876,142, Response filed Sep. 12, 2018 to Restriction Requirement dated Jul. 13, 2018", 7 pgs.
"U.S. Appl. No. 14/876,142, Response filed Dec. 19, 2018 to Non Final Office Action dated Sep. 28, 2018", 14 pgs.
"U.S. Appl. No. 14/876,142, Restriction Requirement dated Jul. 13, 2018", 7 pgs.
"U.S. Appl. No. 29/484,228, Final Office Action dated Feb. 12, 2015", 7 pgs.
"U.S. Appl. No. 29/484,228, Non Final Office Action dated Sep. 30, 2014", 10 pgs.
"U.S. Appl. No. 29/484,228, Response filed Jan. 30, 2015 to Non Final Office Action dated Sep. 30, 2014", 6 pgs.
"U.S. Appl. No. 29/484,236, Non Final Office Action dated Jun. 3, 2015", 11 pgs.
"Australian Application Serial No. 2012256057, First Examiner Report dated Dec. 1, 2015", 2 pgs.

"Australian Application Serial No. 2012256057, Response filed Apr. 6, 2016 to First Examiner Report dated Dec. 1, 2015", 6 pgs.
"Australian Application Serial No. 2016210631, First Examination Report dated Sep. 30, 2017", 7 pgs.
"Australian Application Serial No. 2016210631, Response filed Nov. 22, 2017 to First Examination Report dated Sep. 30, 2017", 18 pgs.
"Chinese Application Serial No. 201680024942.0, Office Action dated Oct. 9, 2018", (W/ English Translation of Claims), 7 pgs.
"Chinese Application Serial No. 201680024942.0, Response filed Jan. 10, 2019 to Office Action dated Oct. 9, 2018", (W/ English Claims), 7 pgs.
"European Application Serial No. 16710584.0, Response filed May 21, 2018 to Office Action dated Nov. 10, 2017", 15 pgs.
"International Application Serial No. PCT/US2012/037750, International Preliminary Report on Patentability dated Nov. 28, 2013", 9 pgs.
"International Application Serial No. PCT/US2012/037750, International Search Report dated Jul. 4, 2012", 6 pgs.
"International Application Serial No. PCT/US2012/037750, Written Opinion dated Jul. 4, 2012", 7 pgs.
"International Application Serial No. PCT/US2016/020836 International Search Report dated Jul. 8, 2016", 6 pgs.
"International Application Serial No. PCT/US2016/020836 Written Opinion dated Jul. 8, 2016", 11 pgs.
"International Application Serial No. PCT/US2016/020836, International Preliminary Report on Patentability dated Sep. 14, 2017", 12 pgs.
"International Application Serial No. PCT/US2016/020836, Invitation to Pay Additional Fees and Partial Search Report dated May 11, 2016", 8 pgs.
"Japanese Application Serial No. 2014-511440, Office Action dated Apr. 15, 2016", (W/ English Translation), 7 pgs.
"Japanese Application Serial No. 2014-511440, Response filed Jul. 13, 2016 to Office Action dated Apr. 15, 2016", (W/ English Translation), 9 pgs.
U.S. Appl. No. 13/470,630 U.S. Pat. No. 9,161,761, May 14, 2012, Bi-Cruciate Knee System.
U.S. Appl. No. 14/876,142, filed Oct. 6, 2015, Bi-Cruciate Knee System.
U.S. Appl. No. 14/013,859, filed Aug. 29, 2013, Bi-Cruciate Knee System.
U.S. Appl. No. 29/484,236, filed Mar. 7, 2014, Bi-Cruciate Knee System.
U.S. Appl. No. 29/484,228, filed Mar. 7, 2014, Tibial Tray and Bearing.
U.S. Appl. No. 14/639,522, filed Mar. 5, 2015, Bi-Cruciate Knee System.
"U.S. Appl. No. 14/876,142, Notice of Allowance dated Jul. 25, 2019", 9 pgs.
"U.S. Appl. No. 14/876,142, Response filed Jul. 10, 2019 to Final Office Action dated Apr. 11, 2019", 16 pgs.
"Australian Application Serial No. 2016226031, First Examination Report dated Sep. 16, 2019", 2 pgs.
"Canadian Application Serial No. 2,978,210, Examiner's Rule 30(2) Requisition dated Oct. 4, 2019", 4 pgs.
"Canadian Application Serial No. 2,978,210, Response filed Apr. 6, 2020 to Examiner's Rule 30(2) Requisition dated Oct. 4, 2019", 8 pgs.
"Japanese Application Serial No. 2017-546880, Notification of Reasons for Rejection dated Jan. 7, 2020", w/ English Translation, 8 pgs.
"Japanese Application Serial No. 2017-546880, Response filed Apr. 1, 2020 to Notification of Reasons for Rejection dated Jan. 7, 2020", w/ English claims, 21 pgs.

* cited by examiner

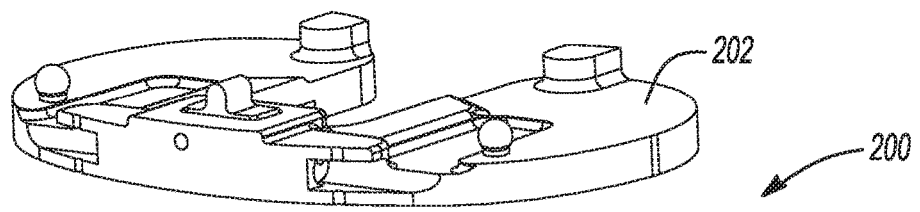
_Fig-30_
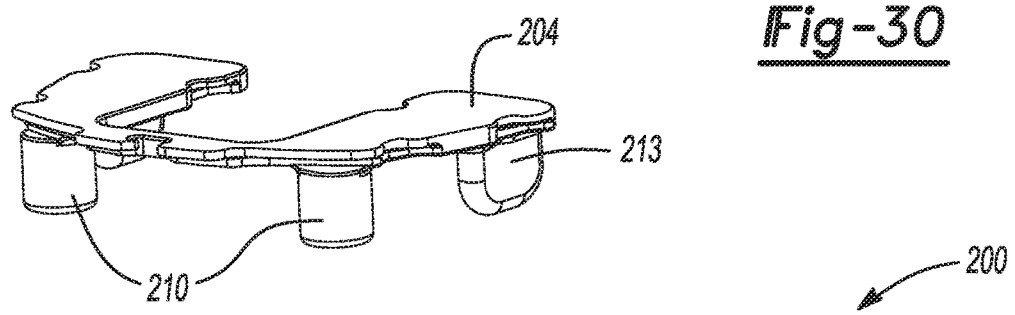
_Fig-31_
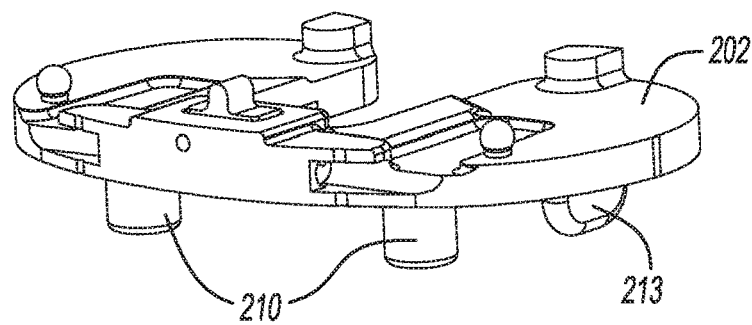
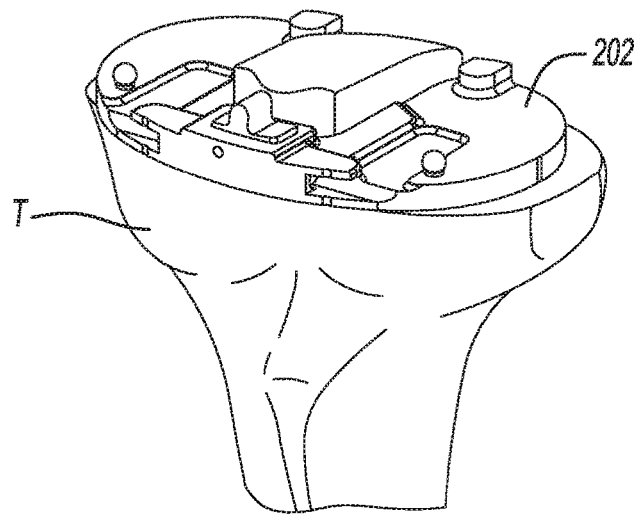
_Fig-32_

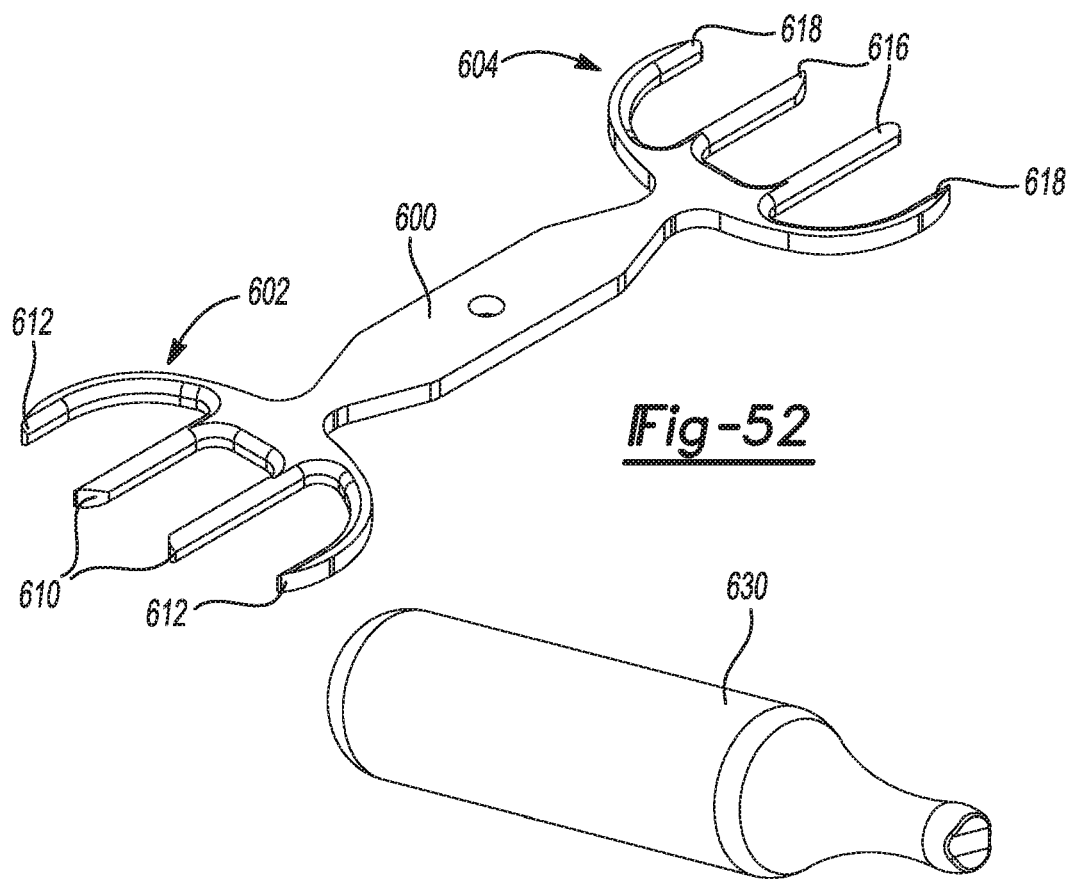
*Fig-52*
*Fig-53*
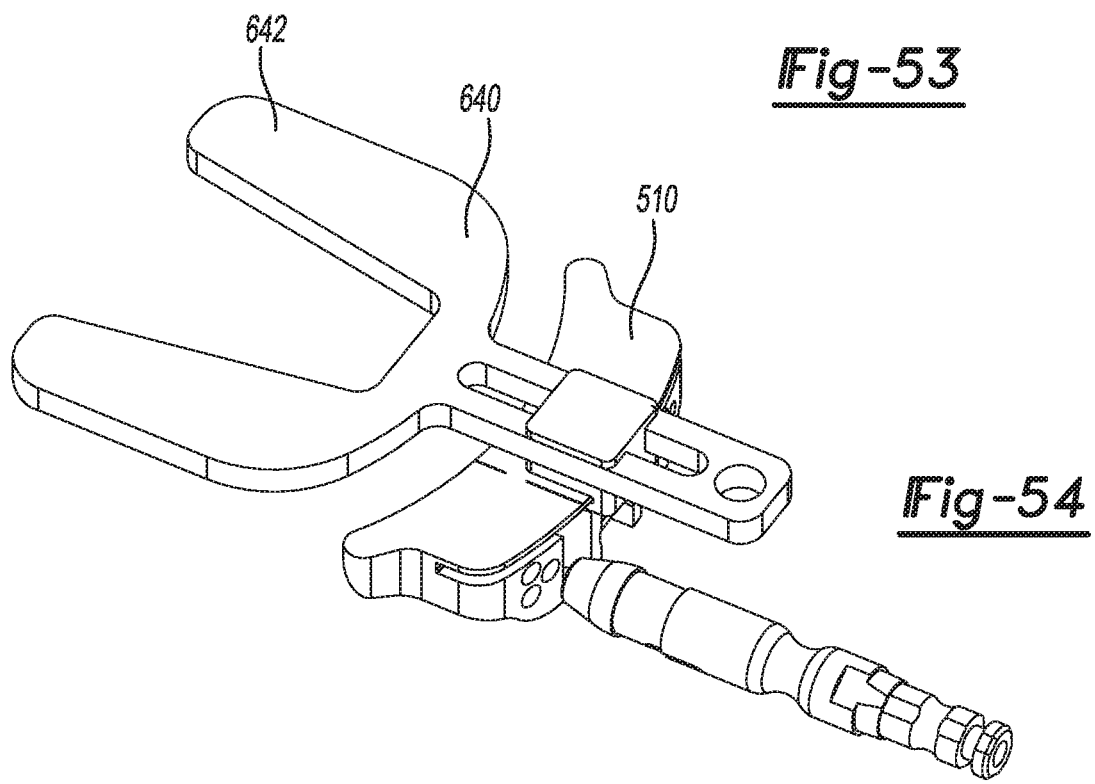
*Fig-54*

BI-CRUCIATE KNEE SYSTEM

CROSS-REFERENCE TO RELATED APPLICATIONS

This application is a continuation-in-part of U.S. patent application Ser. No. 14/013,859 filed on Aug. 29, 2013, which is a continuation-in-part of U.S. patent application Ser. No. 13/470,630 filed on May 14, 2012, which claims the benefit of U.S. Provisional Application No. 61/486,023, filed on May 13, 2011 and 61/593,521, filed on Feb. 1, 2012. This application is also claims the benefit of U.S. Provisional Patent Application No. 61/950,383 filed on Mar. 10, 2014. The entire disclosures of each of the above applications are incorporated herein by reference.

FIELD

The following disclosure relates generally to knee surgery and more specifically to instrumentation, implants, and related method for preparing a knee for a bi-cruciate knee implant.

SUMMARY

This section provides a general summary of the disclosure, and is not a comprehensive disclosure of its full scope or all of its features.

An instrumentation set for preparing a proximal tibia during a bi-cruciate retaining procedure can include a tibial resection block and a stylus. The tibial resection block can be configured to be fixed to an anterior portion of the proximal tibia. The tibial resection block can define a slot that extends in a medial-lateral direction when the tibial resection block is fixed to the proximal tibia. The stylus can have a first block attachment feature and a second block attachment feature. The first block attachment feature can be offset from the stylus a first distance. The second block attachment feature can be offset from the stylus a second distance. The first and second block attachment features of the stylus can be selectively and alternatively received by the slot of the tibial resection block to position the stylus at distinct offset locations relative to the slot.

According to additional features, the first and second attachment features both comprise a lateral projection configured for receipt by the tibial resection block. The first and second block attachment features can oppositely extend from an attachment body. In other features, the instrument set can further include a vertical cut guide having a body, a medial arm and a lateral arm. The medial cut slot can be defined between the body and the medial arm. The lateral cut slot can be defined between the body and the lateral arm. The cut guide can further comprise a tongue extending therefrom. The tongue can be configured to be received by and slidably translate along the slot of the tibial resection block. A locking arm can be coupled to the cut guide and movable between an unlocked position and a locked position. In the unlocked position, the cut guide is permitted to translate relative to the tibial resection block. In the locked position, the locking arm engages the tibial resection block and inhibits movement of the cut guide relative to the tibial resection block. The tibial resection block can provide a seven degree posterior slot cut inclination.

According to other features, the instrument set can further comprise a tibial resection level guide having a handle end, an attachment portion and an engaging end. The attachment portion can be configured to be selectively received by the slot of the tibial resection block to selectively position the engaging end against a distal femoral resection surface. The instrument set can further include a tibial template tool having a first template end and a second template end. The first template end can have first inner fingers and first outer fingers. The second template end can have second inner fingers and second outer fingers. The first inner fingers can be spaced a first distance corresponding to a first tibial island. The second inner fingers can be spaced a second distance corresponding to a second tibial island. The first outer fingers can define a first outer tibial tray footprint. The second outer fingers can define a second outer tibial tray footprint.

An instrument set for preparing a proximal tibia during a bi-cruciate retaining procedure according to another example of the present disclosure can include a tibial resection block, a stylus, a vertical cut guide and a tibial resection level guide. The tibial resection block can be configured to be fixed to an anterior portion of the proximal tibia. The tibial resection block can define a slot that extends in a medial-lateral direction when the tibial resection block is fixed to the proximal tibia. The stylus can have a first block attachment feature that is offset from the stylus a first distance. The first block attachment feature of the stylus is selectively received by the slot of the tibial resection block to position the stylus at an offset location relative to the slot. The vertical cut guide can have a body, a medial arm and a lateral arm. A medial cut slot can be defined between the body and the medial arm. A lateral cut slot can be defined between the body and the lateral arm. The cut guide can further comprise a tongue that is configured to be received by and slidably translate along the slot of the tibial resection block. The tibial resection level guide can have a handle end, an attachment portion and an engaging end. The attachment portion can be configured to be selectively received by the slot of the tibial resection block to selectively position the engaging end against a distal femoral resection surface. All of the stylus, the vertical cut guide and the tibial resection level guide are selectively and alternatively received by the slot of the tibial resection block.

According to additional features the stylus further includes a second block attachment feature. The second block attachment feature can be offset from the stylus a second distance. The first and second block attachment features of the stylus are selectively and alternatively received by the slot of the tibial resection block to position the stylus at distinct offset locations relative to the slot. The first and second attachment features can both comprise a lateral projection configured for receipt by the tibial resection block. The first and second block attachment features can oppositely extend from an attachment body.

In other features, the vertical cut guide can further comprise a locking arm coupled to the cut guide and movable between an unlocked position and a locked position. In the unlocked position, the cut guide is permitted to translate relative to the tibial resection block. In the locked position, the locking arm engages the tibial resection block and inhibits movement of the cut guide relative to the tibial resection block. The instrument set can further include a tibial template tool having a first template end and a second template end. The first template end can have first inner fingers and first outer fingers. The second template end can have second inner fingers and second outer fingers. The first inner fingers are spaced a first distance corresponding to a first tibial island. The second inner fingers are spaced a second distance corresponding to a second tibial island. The first outer fingers can define a first outer tibial tray footprint. The second outer fingers can define a second outer tibial tray footprint.

A method for preparing a proximal tibia for receipt of a bi-cruciate implant includes determining a resection level of the proximal tibia. A tibial cut block can be fixed relative to the proximal tibia based on the determination. The tibial cut block can have a slot defined thereon. A vertical cut guide can be located at the slot. The vertical cut guide can have a medial slot and a lateral slot. A vertical medial cut and a vertical lateral cut can be prepared into the proximal tibia while referencing the respective medial and lateral slots. The vertical cut guide can be removed from the slot. An attachment extending from a tibial resection level guide can be inserted into the slot. A depth of resection of the tibia can be verified with the tibial resection level guide.

According to one example paddles extending from the tibial resection guide can be engaged against a femoral surface to verify the depth of resection of the tibia. A preferred offset between a stylus and the tibial resection block can be determined. One of (i) a first block attachment feature provided on the stylus and (ii) a second block attachment feature provided on the stylus can be selected. The first block attachment feature can be offset a first distance from the stylus. The second block attachment feature can be offset a second distance from the stylus. The first and second distances can be distinct. The selected first or second block attachment feature can be mated to the slot of the tibial resection block. The vertical cut guide can be slidably translated along the slot defined in the tibial cut block until a desired medial-lateral position relative to the proximal tibia has been attained. The vertical cut guide can be fixed to the tibial cut block based on attaining the desired medial-lateral position. Fixing can include moving a locking arm extending from the vertical cut guide from an unlocked position to a locked position. In the locked position, a finger extending from the arm engages the tibial cut block.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 30 is a front perspective view of a tibial tray trial and tibial tray trial insert constructed in accordance to one example of the present teachings.

FIG. 31 is a front perspective view of the tibial tray trial and tibial tray trial insert shown in an assembled position.

FIG. 32 is an anterior perspective view of the prepared proximal tibia shown with the tibial tray trial and tibial tray trial insert located thereon.

FIG. 52 is a front perspective view of a tibial template tool constructed in accordance to one example of the present disclosure;

FIG. 53 is a front perspective view of a holding tool constructed in accordance to one example of the present disclosure;

FIG. 54 is a front perspective view of a tibial recutting guide constructed in accordance to one example of the present disclosure;

Corresponding reference numerals indicate corresponding parts throughout the several views of the drawings.

DETAILED DESCRIPTION

Figure 1:
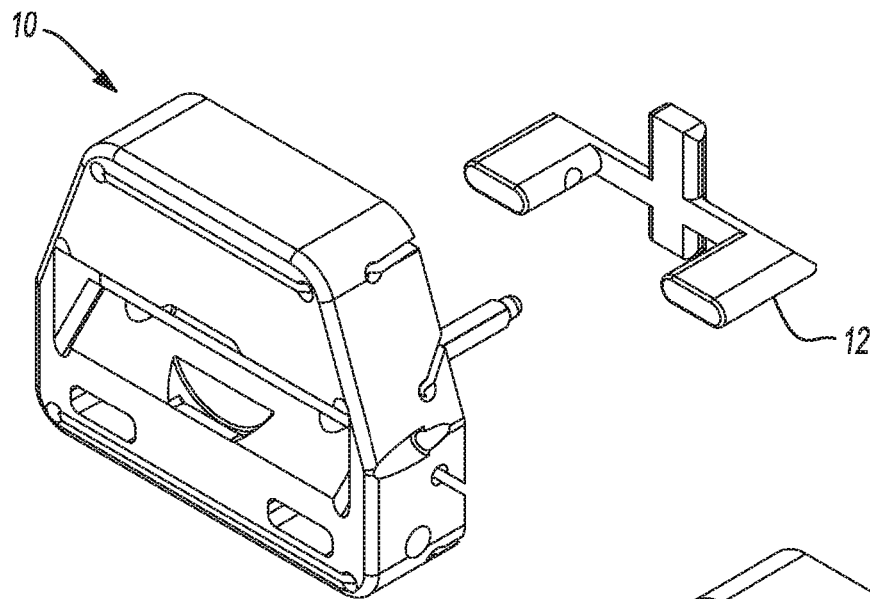
FIG. 1 is a perspective view of an exemplary 4-in-1 cutting block shown with a selectively attachable ACL protector.

The following description will focus on preparation of a left knee for receipt of a bi-cruciate knee implant. In this regard, the following description will be directed toward various methods and techniques using instrumentation for preparing a left knee using a bi-cruciate knee system. It will be appreciated however, that the same may be adapted for use with a right knee.

While the intended focus of the instant application will be directed specifically to preparation of the tibia and related implants, a brief description of an exemplary preparation of a left femur will be described. In order to assess bone stock, potential ligament instability and the anatomical axis, a standing anterior/posterior x-ray may be used. In some examples, a 36 inch long standing anterior/posterior x-ray may be used. Initially, the angle between the anatomic and mechanical axis may be determined while assuring that the distal femoral cut is perpendicular to the mechanical axis. At this time, the femoral component size may be estimated pre-operatively by using lateral view x-rays and radio graphic templates. The appropriate size femoral component may be confirmed intra-operatively.

An intramedullary (IM) drill may be used to penetrate the intracondylar notch and dense cancellous bone of the distal femur to a depth of approximately 1.5-2 inches (3.5-5 centimeters). A 0.375 inch drill may be used to penetrate the distal femur. The canal entry location may be placed one centimeter above the insertion of the posterior cruciate ligament and slightly medial in the intracondylar notch. The appropriate left or right valgus wing may be chosen and slid onto the IM rod. The IM rod may be introduced into the femoral canal to de-pressurize the canal. The valgus wing may be slid until it rests against the medial distal condyle. The Slidex® Distal Resection Block and cut block adapter are both slid into the anterior holes of the valgus wing until the Slidex® Distal Resection Block contacts the anterior cortex of the femur.

To confirm the valgus angle, the alignment handle can be inserted into the cut block adapter and a ⅝ inch alignment rod can be inserted and extended to the center of the femoral head. The Slidex® Distal Resection Block can then be pinned into place using ⅛ inch quick release drill pins in the most proximal pin holes of the block. The valgus wing can then be removed by removing the IM rod and pulling the valgus wing and cut block adapter distally away from the distal resection block leaving the Slidex® Distal Resection Block in place. Two resection slots of 0 or +3 mm are available for the distal resection. The 0 mm slot will resect 9 mm from the most prominent part of the medial distal condyle. If additional distal resection is required, the +3 mm slot will resect 12 mm. If additional distal resection is required beyond the +3 mm slot, the resection guide can be shifted proximally by utilizing the +2 or +4 mm ⅛ inch pin holes. A 0.054 inch saw blade can be used to complete the distal resection through the selected slot. The resected distal femur can be checked by using a flat instrument. The bone surface may be re-cut or filed as necessary to ensure proper resection. For additional stability, the femoral block handle can be utilized.

An exemplary method of femoral sizing will now be described. Initially, the adjustable anterior/posterior sizer may be placed against the resected distal surface with the feet in contact with the posterior condyles of the femur. In a first option, fixed rotation feet may be used. In another option, adjustable rotation feet may be used. An adjustable dial can be used with the anterior/posterior sizer. The adjustable rotation feet are available in left and right varieties with the ability to set an external rotation from 0 to 10 degrees. In one example, it is recommended that an initial setting of 3 degrees of rotation be utilized. The femoral component size can now be read from the central scale. If the size indicated is in between standard sizing or a larger flexion gap is desired, a choice may be made to choose the smaller size and shift the femoral 4-in-1 block placement anteriorly. In order to shift the component anteriorly, a screw mechanism in the central portion of the sizer is turned which raises the level of drill holes in one millimeter increments. A scale is located on the sizer to indicate how far the component will be anteriorly shifted. If medial/lateral width is a concern, the appropriately sized medial/lateral width checker can be inserted into the anterior/posterior sizer to further evaluate the proper size of the femur. Next, two 4-in-1 cutting block location holes are drilled utilizing a ⅛ inch drill pin. In one example, the final medial/lateral position of the femoral component is not determined during this step, but is addressed later in the technique.

Figure 2:
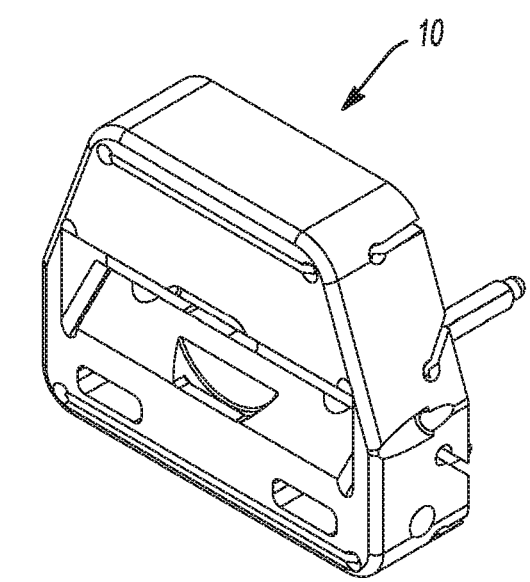
FIG. 2 is a perspective view of the 4-in-1 block of FIG. 1.

With initial reference now to FIGS. 1 and 2, initial preparation of the distal femur using a 4-in-1 block 10 according to the present teachings will be described. At the outset, a surgeon may choose the desired 4-in-1 block 10 that matches the selected size on the anterior/posterior sizer and place it into the ⅛ inch holes drilled into the distal femur. A 0.054 inch feeler blade can be used to determine the amount of anterior bone resection. If the feeler blade indicates a probability of notching, an anterior/posterior femoral shift block may be used to adjust the cut block holes anteriorly in one millimeter increments. Notably, moving the block anteriorly will resect additional posterior condylar bone. ⅛ inch pins can be placed in the side holes provided on the femoral 4-in-1 block 10. The anterior/posterior block must be sitting flush against the distal femur at this point. An ACL protector 12 may be secured into place relative to the 4-in-1 block 10. The ACL protector 12 can be used to block the blade from inadvertently cutting the ACL. Once the position of the 4-in-1 block 10 is satisfactory, a surgeon can resect the anterior and posterior bone, and the anterior and posterior chamfers using a 0.054 inch saw blade. Again, care must be taken not to cut the ACL while making the posterior and posterior chamfer boney resections.

Figure 3:
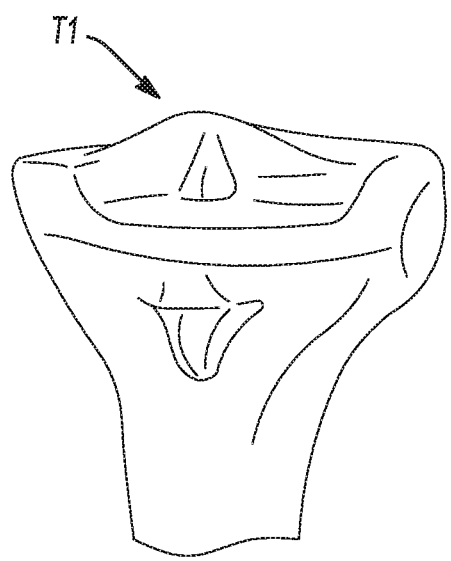
FIG. 3 is an anterior view of an exemplary tibia shown prior to performing tibial preparation.
Figure 4:
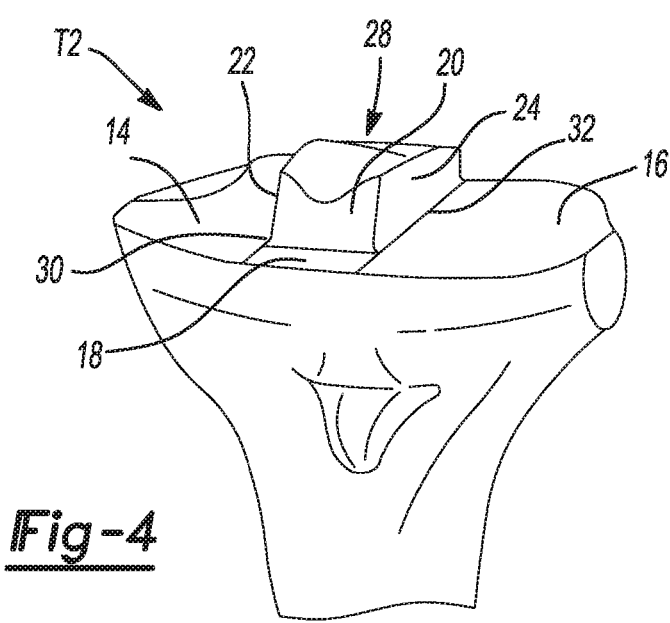
FIG. 4 is an anterior view of the tibia of FIG. 3 and shown subsequent to the tibial preparation.
Figures 5, 6:
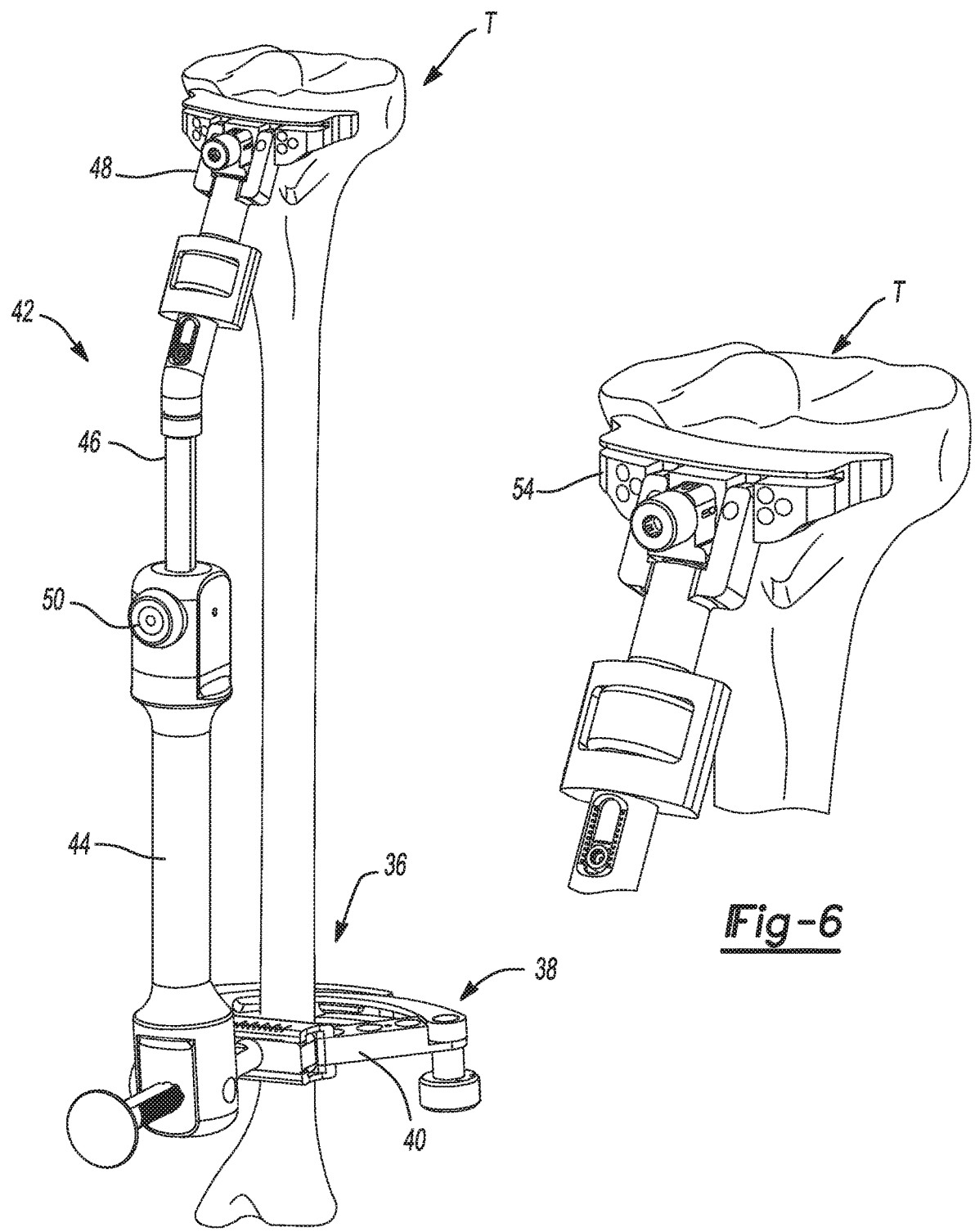
FIG. 5 is an anterior perspective view of the tibia shown with an extramedullary tibial resection guide attached thereto.
FIG. 6 is an anterior perspective view of the proximal tibia and shown with a tibial resection block coupled to the extramedullary tibial resection guide and located against the proximal tibia.

With reference now to FIGS. 3-37, preparation of a proximal tibia for a bi-cruciate knee system according to a first example will be described. FIG. 3 illustrates a tibia T1 prior to performing the instant surgical technique. FIG. 4 illustrates a tibia T2 subsequent to performing the tibial technique according to the present teachings. Of note, the tibia T2 includes a medial plateau 14, lateral plateau 16, anterior plateau 18, anterior chamfer wall 20, medial vertical wall 22, and lateral vertical wall 24. The anterior chamfer wall 20, the medial vertical wall 22, and the lateral vertical wall 24 can collectively cooperate to form an ACL island 28. A radius 30 is formed at a transition between the medial plateau 14 and the medial vertical wall 22. Similarly, a radius 32 is formed at a transition between the lateral plateau 16 and the lateral vertical wall 24.

With reference now to FIGS. 5-29, resection of the tibia T will be described. With the knee flexed, spring loaded arms 36 and 38 of an ankle clamp 40 are located around the distal tibia T just around the malleoli. The ankle clamp 40 can generally be attached to an extramedullary tibial resection guide 42. The extramedullary tibial resection guide 42 can further comprise a handle portion 44, a telescoping rod portion 46, and a resection block connecting portion 48. A button 50 can be provided on the extramedullary tibial resection guide 42 that can control telescoping action of the rod portion 46 generally from the handle portion 44.

Figure 8:
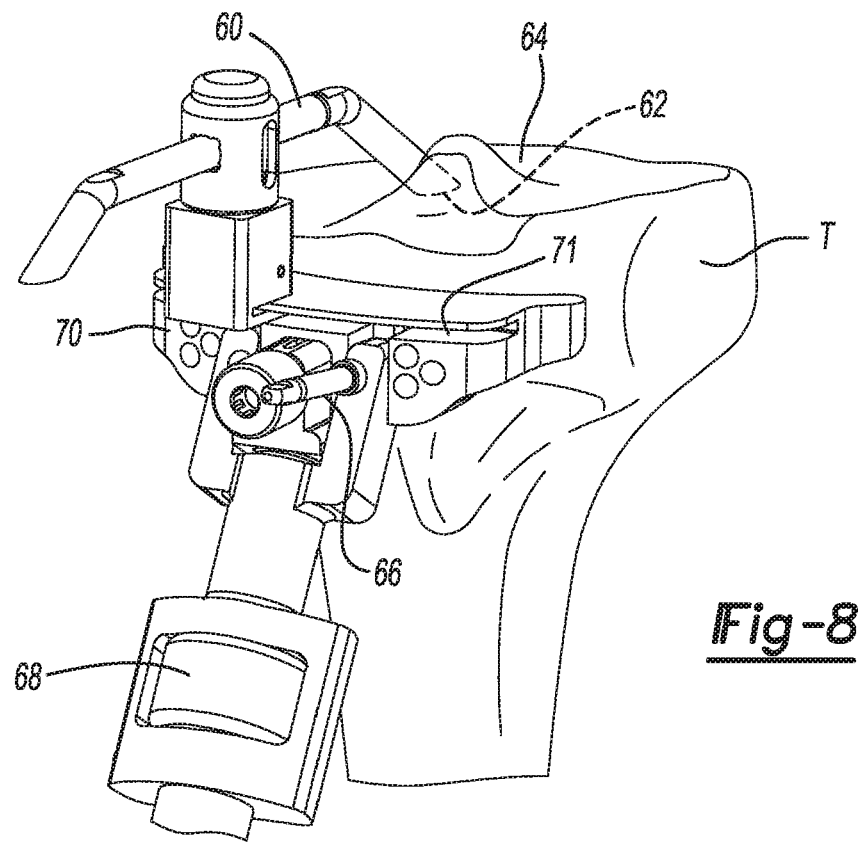
FIG. 8 is an anterior perspective view of the proximal tibia shown with the modular stylus positioned with a terminal end of the modular stylus engaged to the lowest point of the medial tibial plateau.
Figure 9:
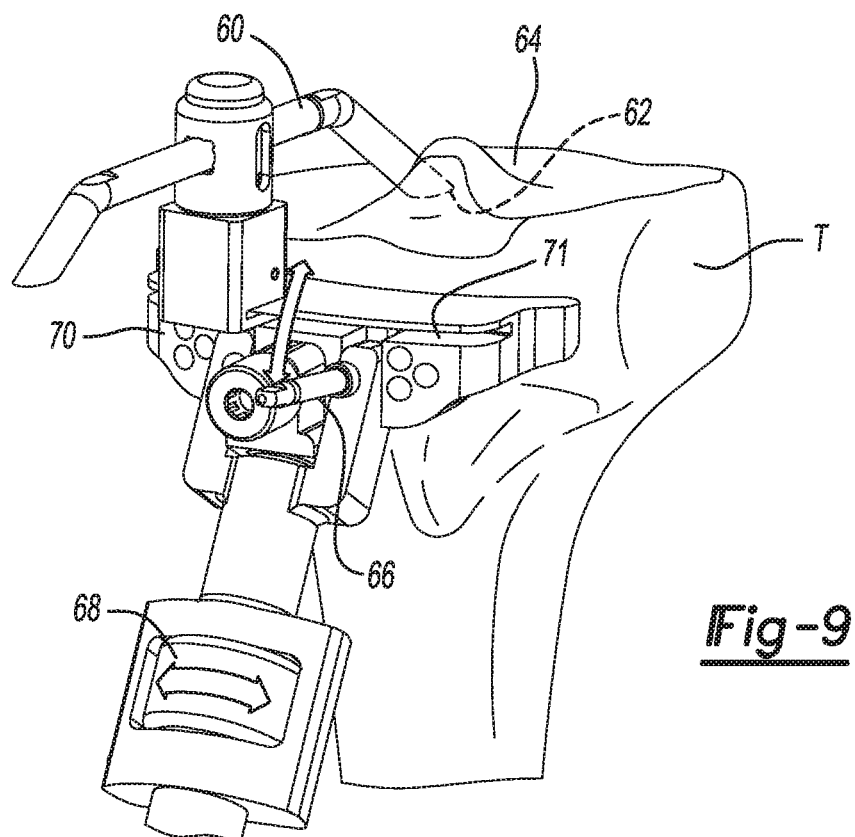
FIG. 9 is an anterior perspective view of the proximal tibia of FIG. 8 shown with the tibial resection block coupled with a modular stylus being adjusted to a desired location.

At this point, a tibial resection block 54 (FIG. 6) can be placed against the proximal tibia T. Returning now to FIG. 5, from the sagittal view, the side of the extramedullary tibial resection guide 42 is adjusted such that it is generally parallel with the shaft of the tibia T. The tibial resection block is set at 4 degrees of slope (other measurements may be used) when attached to the extramedullary guide. Once adjustment of the resector axis is correct in the medial/lateral view, the resection block connecting portion 48 is rotated until the shaft of the resector is just medial to the tibial tubercle. Using a stylus 60 (FIGS. 7 and 8), the extramedullary tibial resection guide 42 is adjusted such that a terminal end 62 of the stylus 60 is engaged to a lowest point of the medial tibial plateau 64. Using a ⅛ inch pin 66, the extramedullary tibial resection guide 42 is secured to the tibia T. A dial 68 may be used to fine tune the resection level prior to making any cut (FIG. 9).

Figure 10:
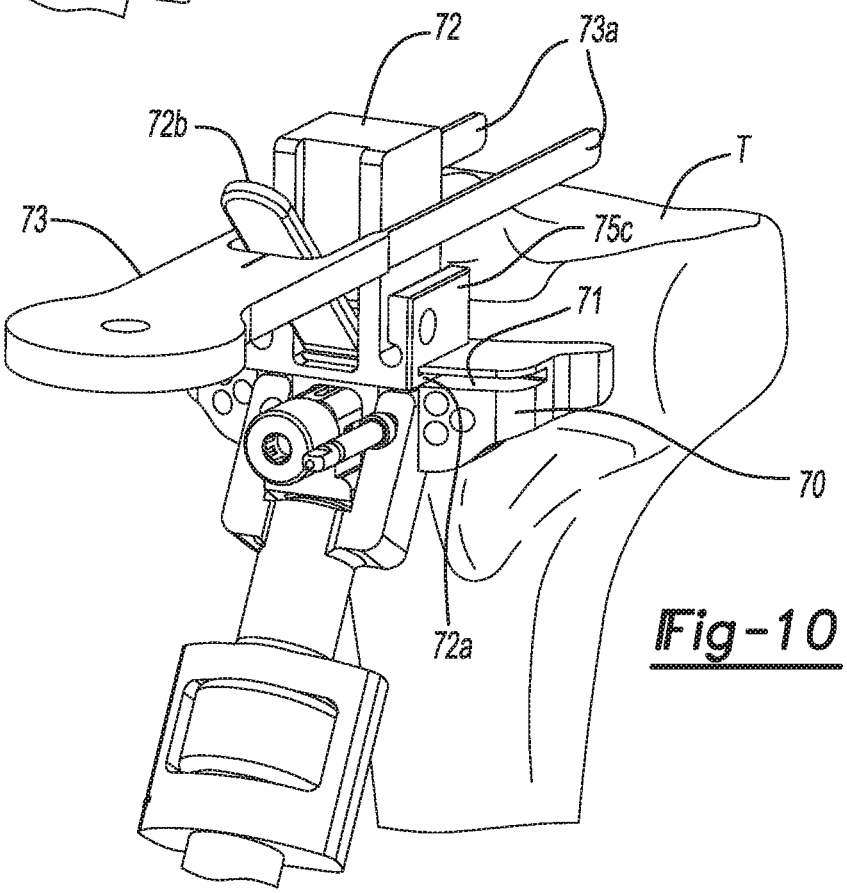
FIG. 10 is an anterior perspective view of the proximal tibia shown with a vertical cut guide coupled to the tibial resection block in line with an ACL and tibial island.
Figure 11:
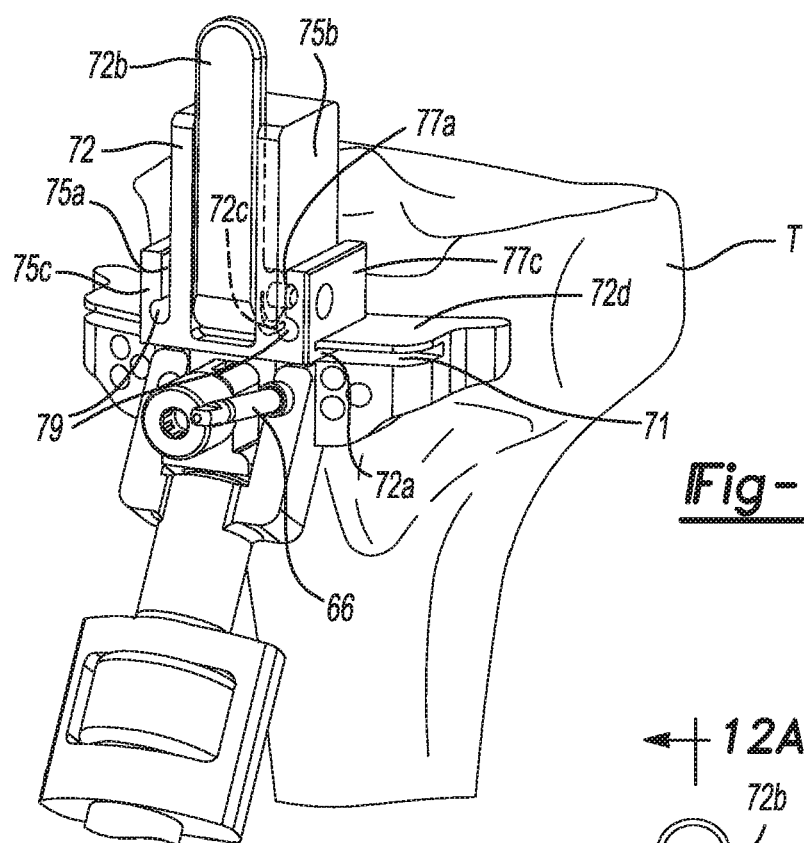
FIG. 11 is an anterior view of the tibia of FIG. 10 and shown with the vertical cut guide coupled to the tibial resection block in a locked position.

Of note, the stylus 60 is set for a 4 mm resection. Prior to pinning the extramedullary tibial resection guide 42 in place, make sure to allow for adjustability of the height of a tibial resection cut block 70. The tibial resection cut block 70 can define a horizontal slot 71. Once the resection level is set, the stylus 60 can be removed. A vertical cut guide 72 can then be attached to the tibial resection cut block 70 (FIG. 10).

The vertical cut guide 72 can then be adjusted to an appropriate position (in a medial/lateral direction along the slot 71) to make the desired vertical cuts. Specifically, a tongue 72a extending from the vertical cut guide 72 can slide along the slot 71. An alignment guide 73 can be used to aid in the positioning of the vertical cut guide 72. The alignment guide 73 generally includes a pair of parallel and elongated arms 73a that slidably locate on opposite sides of the vertical cut guide 72. Of note, the vertical cuts will determine the final tibial component rotation. It is important to leave equal amounts of bone on the medial and lateral aspect of the ACL fibers. At this point, the vertical cut guide 72 can be clamped in place by rotating a locking arm 72b from an unlocked position shown in FIG. 10 to a locked position shown in FIGS. 11 and 12. In one example, the locking arm 72b can have a finger 72c that rotates into fixed engagement with an upper surface 72d of the cut block 70. With a reciprocating saw, a vertical medial cut 74 can be prepared while passing a saw through a medial slot 75a defined between a main body 75b of the vertical cut guide 72 and a medial arm 75c. The vertical medial cut 74 may be prepared while referencing a medial surface 75 of the vertical cut guide 72. It will be appreciated that the vertical medial cut 74 may be prepared while concurrently referencing the medial arm 75c. After the vertical medial cut 74 has been prepared, the vertical lateral cut may be made. The vertical lateral cut 76 can be prepared while passing a saw through a lateral slot 77a defined between the main body 75b of the vertical cut guide 72 and a lateral arm 77c. The vertical lateral cut 76 may be prepared while referencing a lateral surface 77 of the vertical cut guide 72. It will be appreciated that the vertical lateral cut 76 may be prepared while concurrently referencing the lateral arm 77c. Headless vertical pins 78 can be located through partial bores 79 (FIGS. 11 and 12) provided in the vertical cut guide 72 driven into the anterior tibia T. The vertical medial cut 74 and the vertical lateral cut 76 can both be prepared using a saw blade having teeth or cutting structure consistent for forming the radius cuts 30 and 32 identified in FIG. 4. Notably, by incorporating a radius at this transition, the bone at the transition between the respective medial and lateral plateaus 14, 16 and ACL island 28 (FIG. 4) can be stronger as compared to a transverse, 90 degree intersecting cut. Next, the vertical cut guide 72 is removed from the headless vertical pins 78. The medial side of the tibia T may then be horizontally resected.

Figure 12:
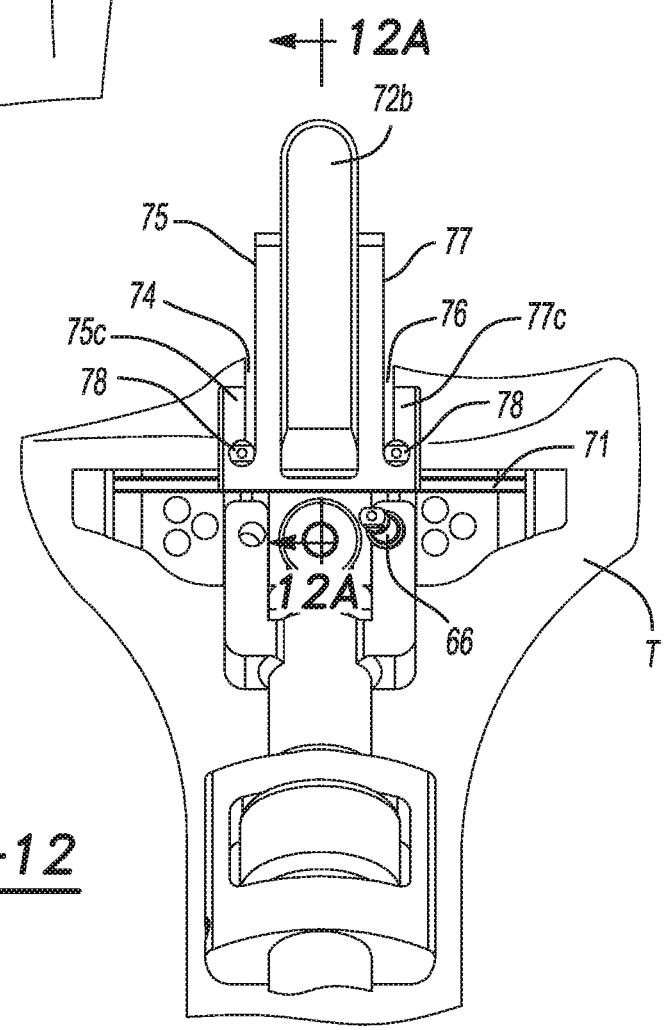
FIG. 12 is an anterior view of the proximal tibia shown subsequent to performing a pair of vertical cuts that will form lateral and medial sides of an ACL island made while referencing the vertical cut guide.
Figure 12A:
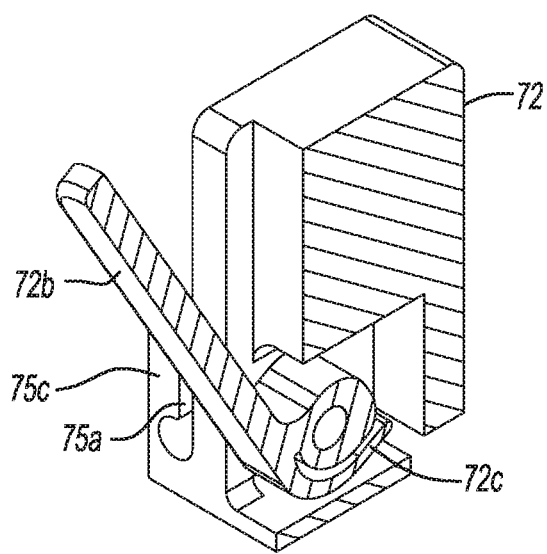
FIG. 12A is a cross-sectional view taken along lines 12A-12A of FIG. 12.
Figure 12B:
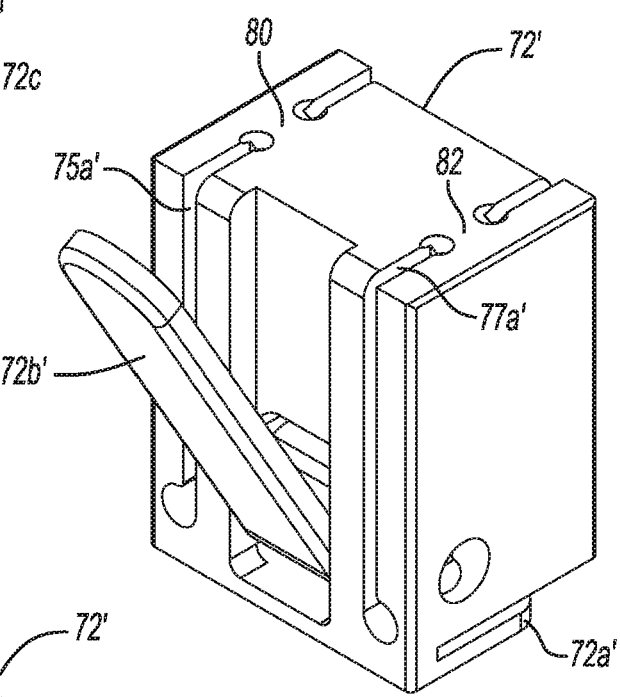
FIG. 12B is a perspective view of a vertical cut guide constructed in accordance to additional features.
Figure 12C:
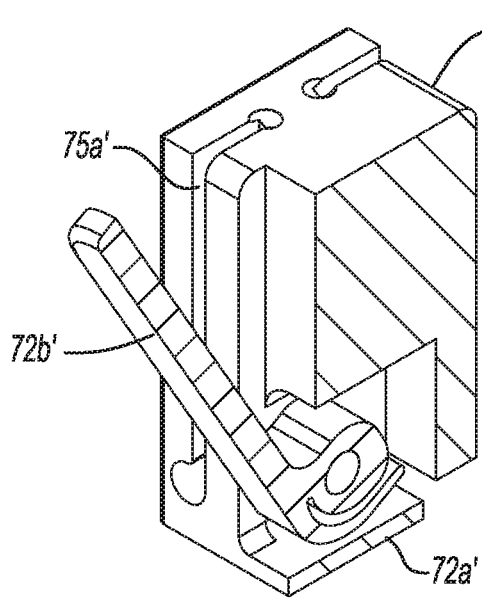
FIG. 12C is a cross-sectional view of the vertical cut guide of FIG. 12B.

With reference to FIG. 12A, a cross-sectional view of the cut guide 72 is shown. FIGS. 12B and 12C show an alternate vertical cut guide 72'. Unless otherwise described herein, the cut guide 72' incorporates similar features as the cut guide 72 that are identified with like reference numerals having a prime suffix. The cut guide 72' provides a captured vertical medial slot 75a' and a captured vertical lateral slot 77a'. Specifically, an upper medial wall 80 and an upper lateral wall 82 close the respective vertical medial slot 75a' and the vertical lateral slot 77a'. The upper medial and lateral walls 80 and 82 can assist in maintaining a saw blade within the respective medial and lateral slots 75a' and 77a'.

Figure 13:
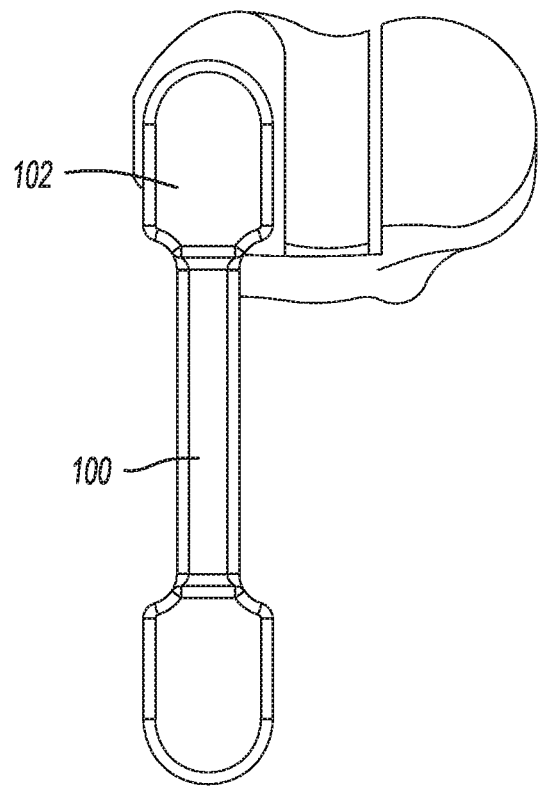
FIG. 13 is a superior view of the proximal tibia shown with a pre-trial spacer located atop of the lateral plateau to verify the height of tibial bone that was resected.
Figure 14:
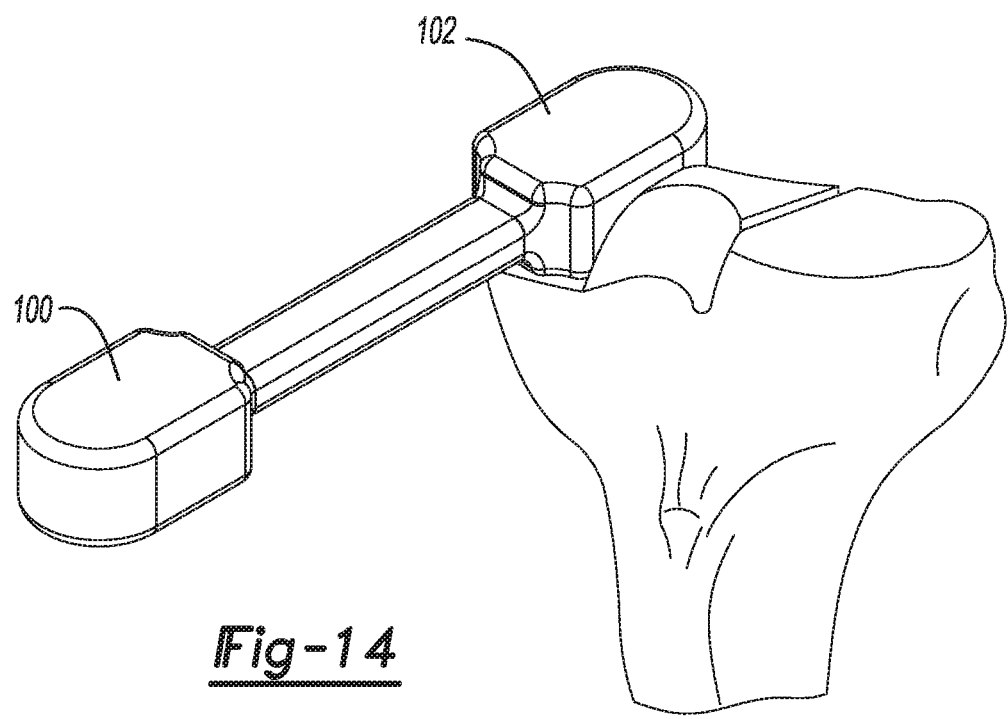
FIG. 14 is an anterior perspective view of the proximal tibia and pre-trial spacer shown in FIG. 13.

At this point, the medial side gap may be verified in extension using an 8/9 mm spacer block 100 (FIGS. 13-14). If the 9 mm spacer portion 102 is too tight, additional tibial bone will need to be removed. This can be done by simply dialing the resection block down 1 mm. Once the medial side extension gap is adequate, the lateral side of the tibia T is horizontally resected with the headless vertical pins 78 left in place. The headless vertical pins 78 protect against undercutting the ACL island 28.

Figure 15:
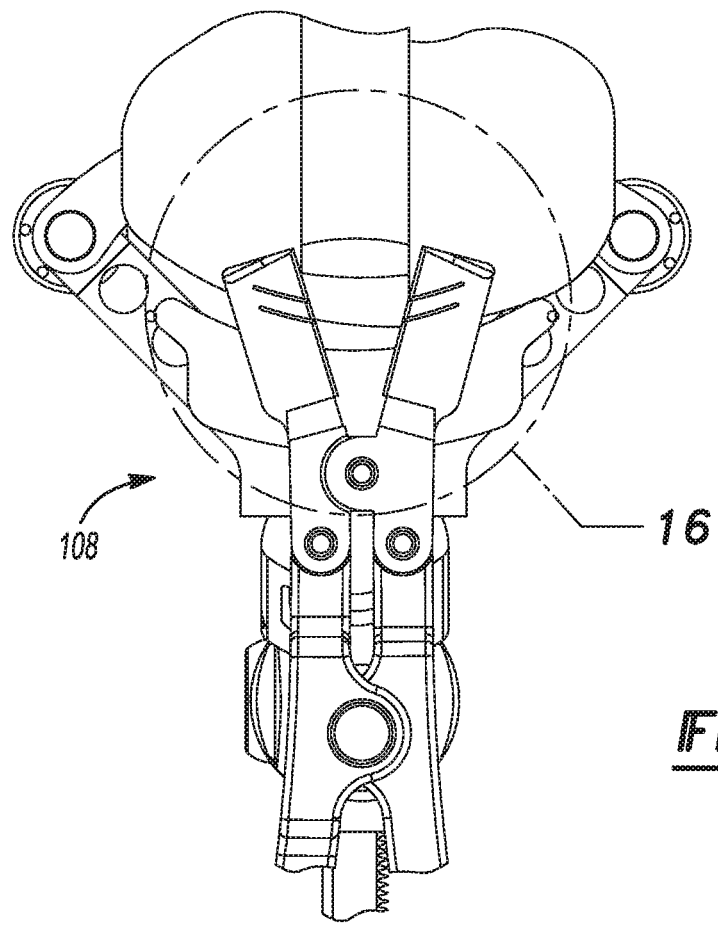
FIG. 15 is a superior view of the proximal tibia shown with a Rongeur tool initially located for resection of the anterior portion of the tibia.
Figure 16:
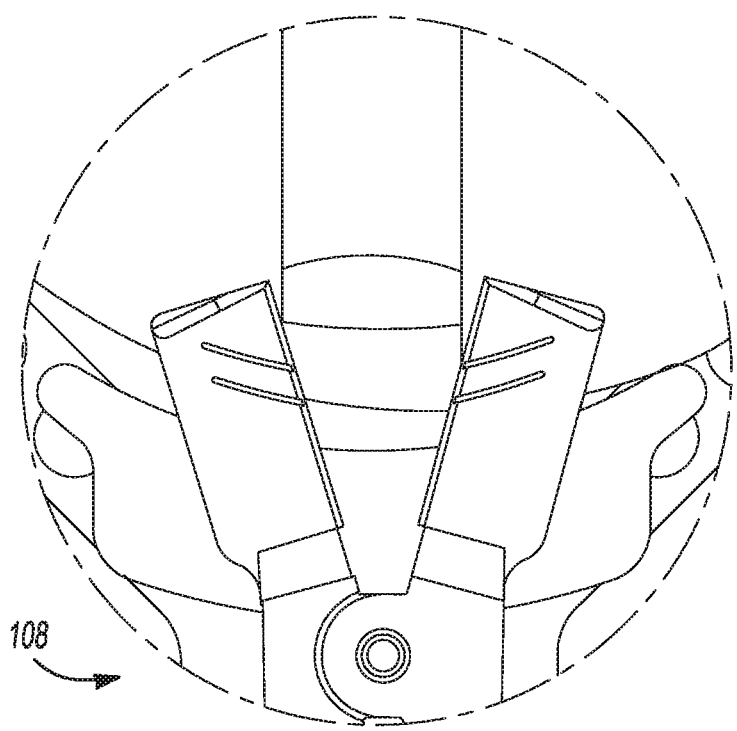
FIG. 16 is a close-up view of the anterior portion of the ACL island of FIG. 15.
Figure 17:
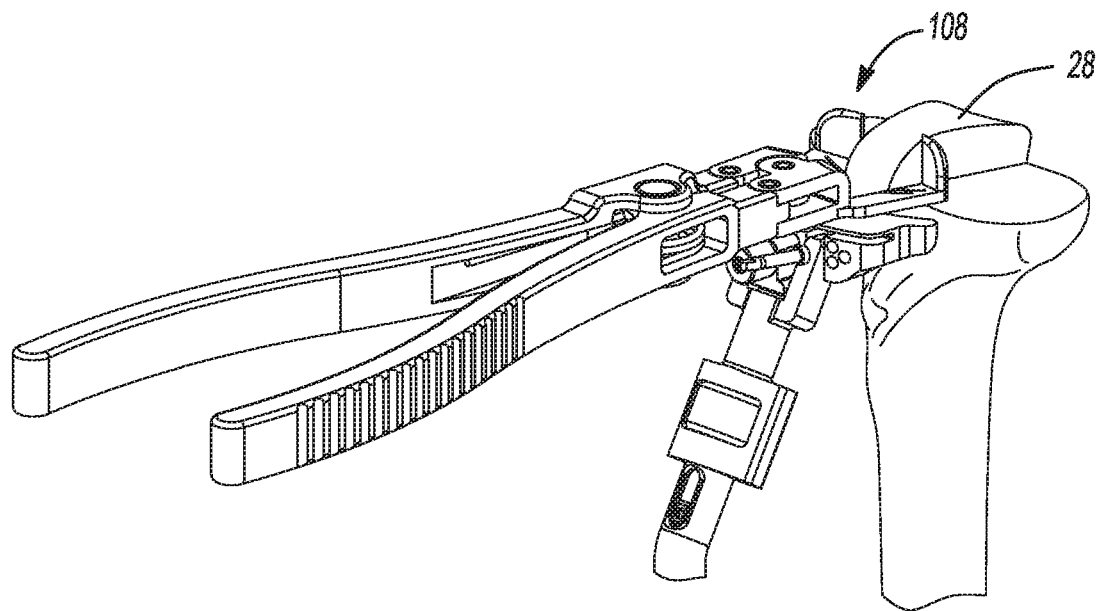
FIG. 17 is an anterior perspective view of the proximal tibia of FIG. 15.
Figure 18:
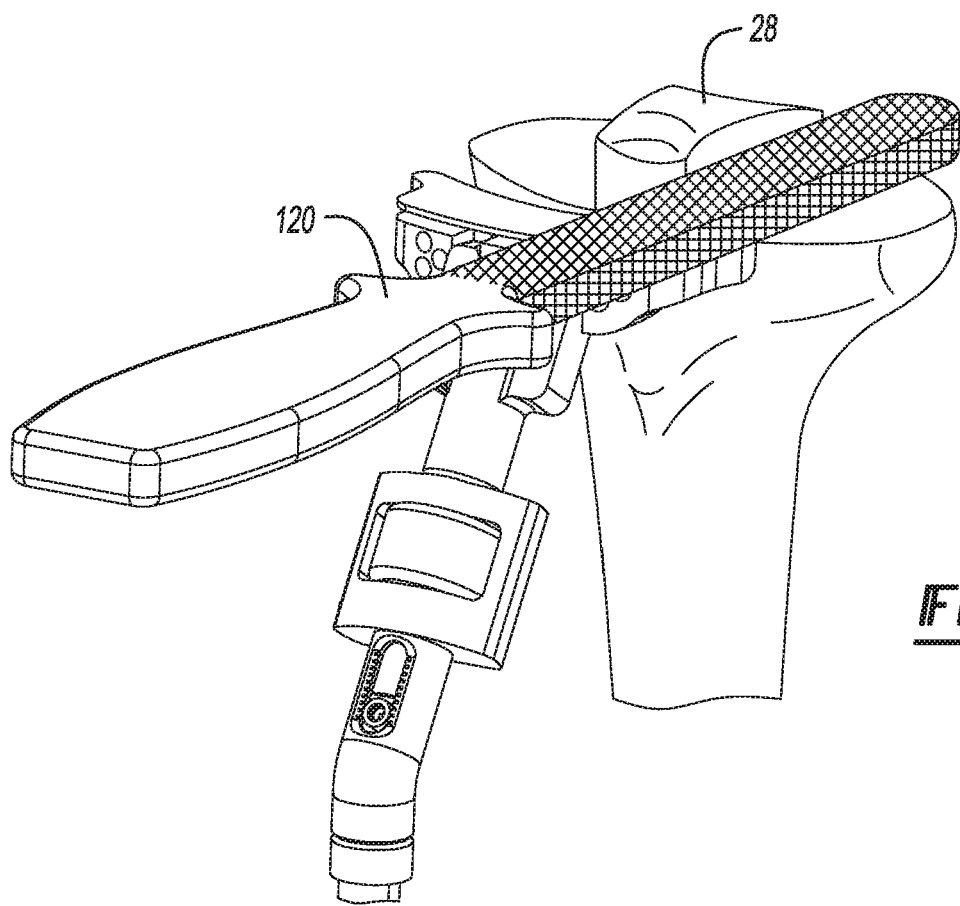
FIG. 18 is an anterior perspective view of the tibia of FIG. 17 and shown subsequent to resection of the anterior island and using a rasp to clean up the surface surrounding the ACL island.
Figure 19:
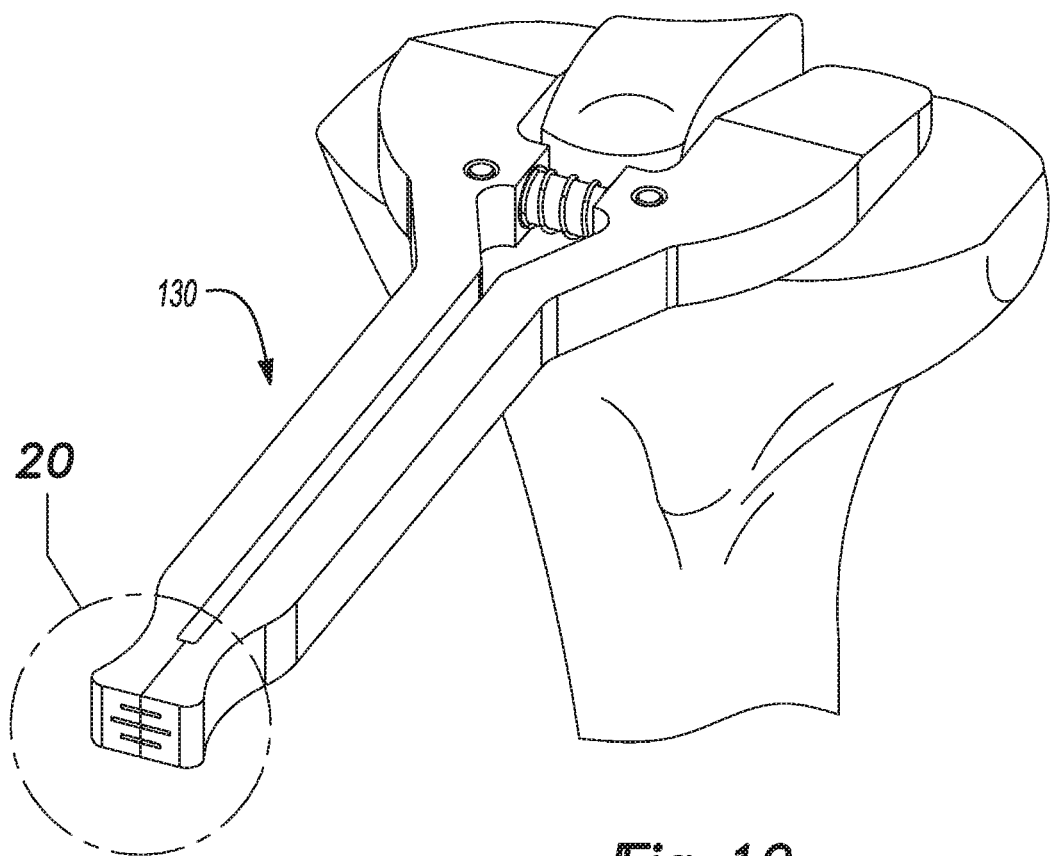
FIG. 19 is an anterior perspective view of the proximal tibia shown with a tibial plateau angle gage disposed thereon.
Figure 20:
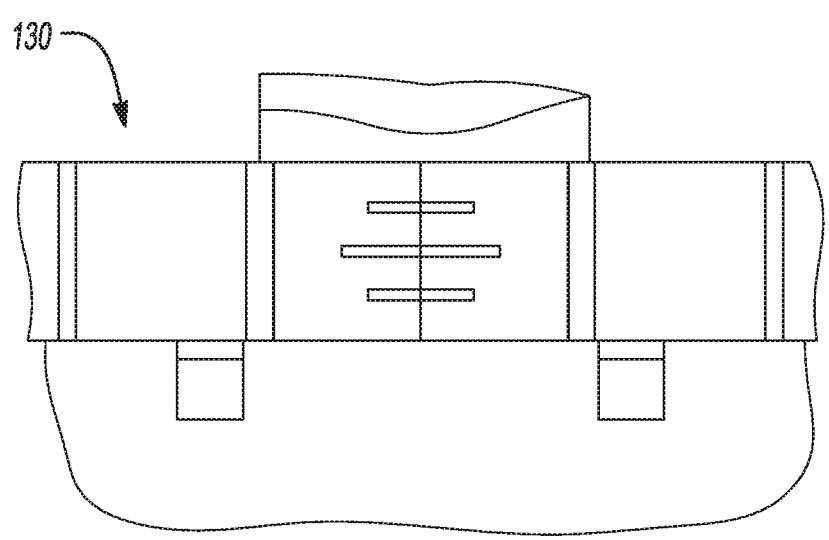
FIG. 20 is a close-up view of a scale of the tibial plateau angle gage of FIG. 19.

As illustrated in FIGS. 15-17, a Rongeur tool 108 can be used to remove the anterior bone making sure to round the corners of the anterior island. Next, an ACL island rasp 120 (FIG. 18) is used to clean the resected tibia T to ensure that there are no rough edges around the ACL island 28 and respective medial and lateral plateaus 14 and 16. Using the tibial plateau angle gage 130 (FIG. 19), the tibial slope cuts are verified to have an equal amount of slope. This will be important for the tibial base plate to be secured properly, and for the proper wear and function of the system.

Figure 21:
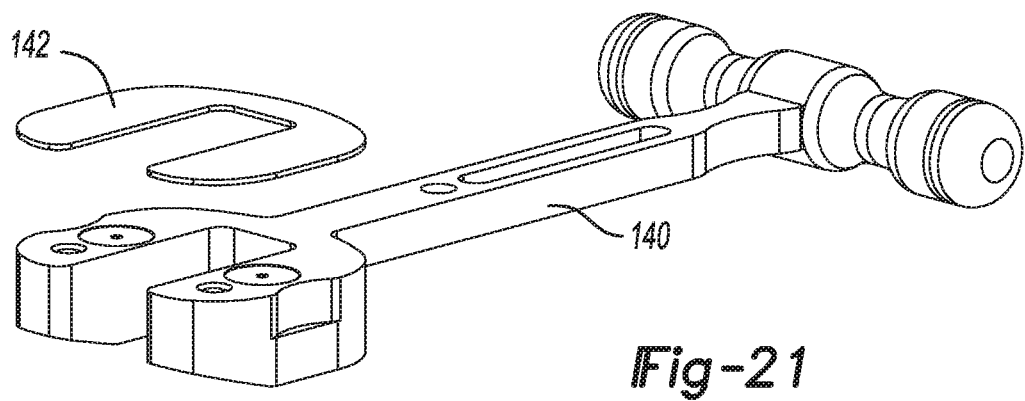
FIG. 21 is a perspective view of a spacer tool used to verify a medial and lateral gap.
Figure 22:
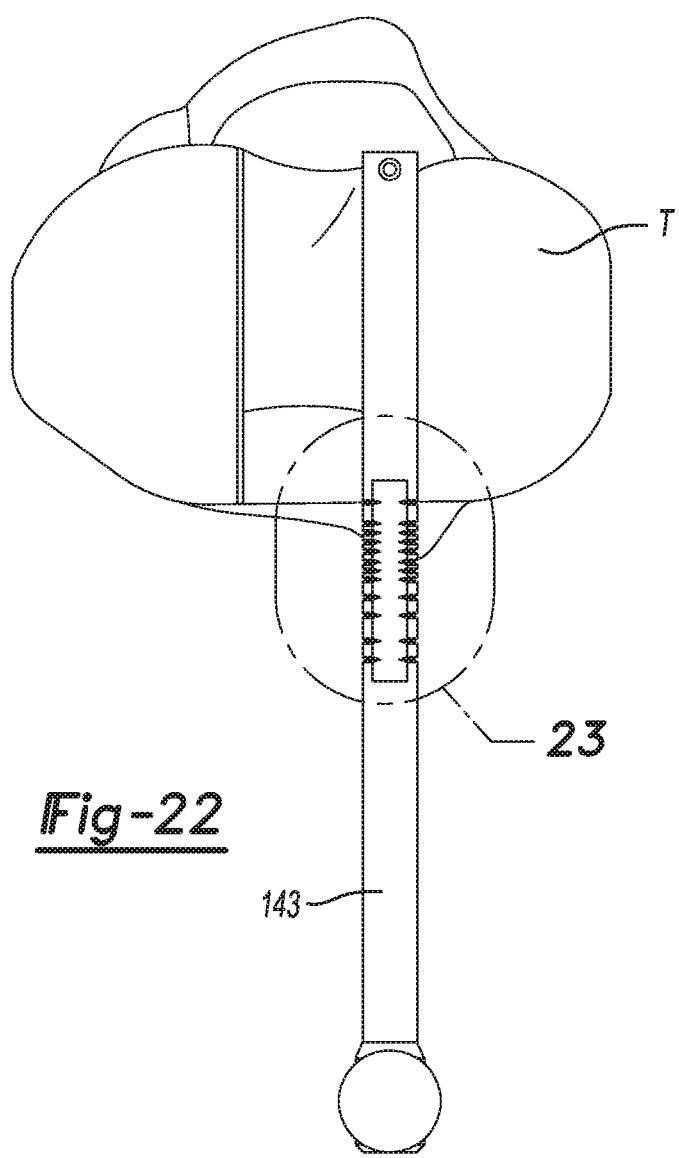
FIG. 22 is a superior view of the proximal tibia shown using an optional anterior/posterior sizer to verify tibia size.
Figure 23:
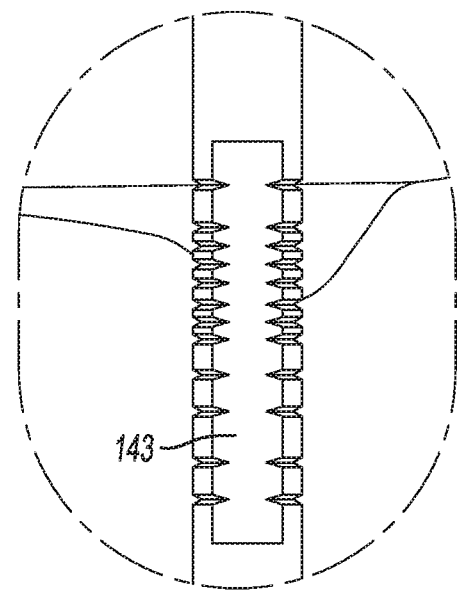
FIG. 23 is a close-up view of a scale of the sizer shown in FIG. 22.

Turning now to FIG. 21, tibial sizing for an intact and functional ACL will be described. The medial and lateral gaps are verified using a spacer tool 140. A series of 1 mm spacers 142 may be magnetically coupled as needed. Rotation and slope may also be verified. Optionally, the tibia T may be sized with an anterior/posterior sizer 143 (FIGS. 22 and 23).

Figure 24:
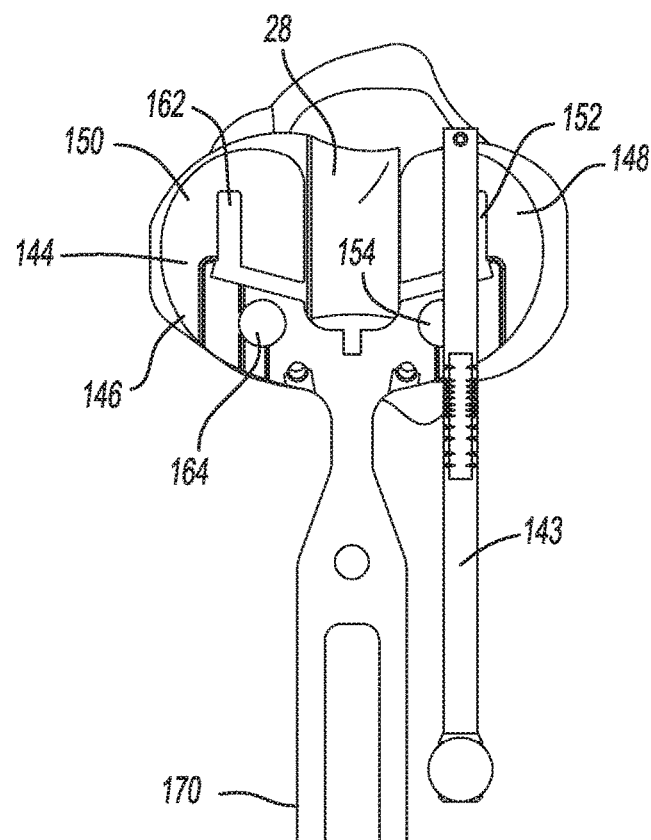
FIG. 24 is a perspective view of the proximal tibia and shown with a tibial template and anterior/posterior sizer disposed thereon used to verify size, rotation and slope.
Figure 25:
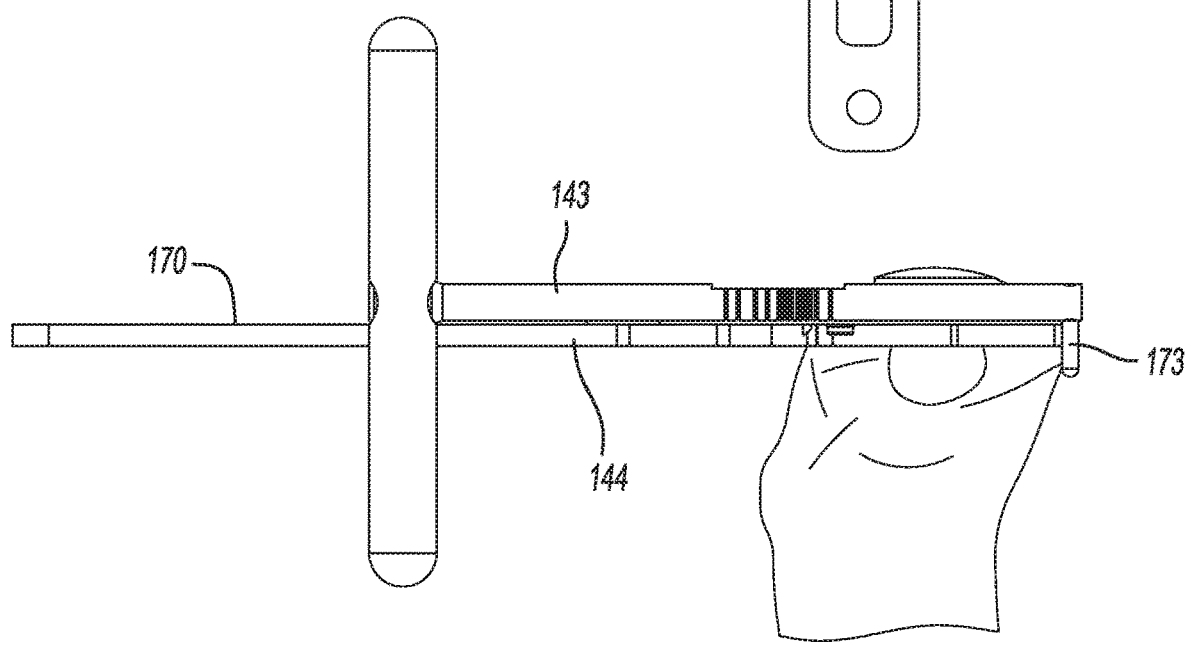
FIG. 25 is a lateral view of the proximal tibia shown with the tibial template and anterior/posterior sizer of FIG. 24 disposed thereon.

The tibia T may then be sized with a tibial template 144 (FIGS. 24-25). The tibial template 144 generally comprises a U-shaped body portion 146 having a lateral side 148, and a medial side 150. A lateral passage 152 and a lateral anterior drill guide 154 can be provided on the lateral side 148. Similarly, a medial passage 162 and medial anterior drill guide 164 can be provided on the medial side 150. Because rotation is determined by the position of the ACL island 28, it is important to check for accurate rotation. Base rotation can be made relative to the tibial tubercle and the malleolar axis. At this point, an extramedullary alignment check can be made by placing a ⅛ inch alignment rod through a handle 170 of the tibial template 144. Slight external rotation is preferred to optimize patellofemoral tracking. Once the final rotation has been determined, the position can be marked by extending anterior marks of the tibial template 144 onto the anterior tibia such as by electrocautery. A locator pin 173 extending from the anterior/posterior sizer 143 can be located around the posterior edge of the tibia T. Extra caution should be used to avoid internal rotation of the tibial template 144 due to the presence of lateral soft tissue.

Figure 26:
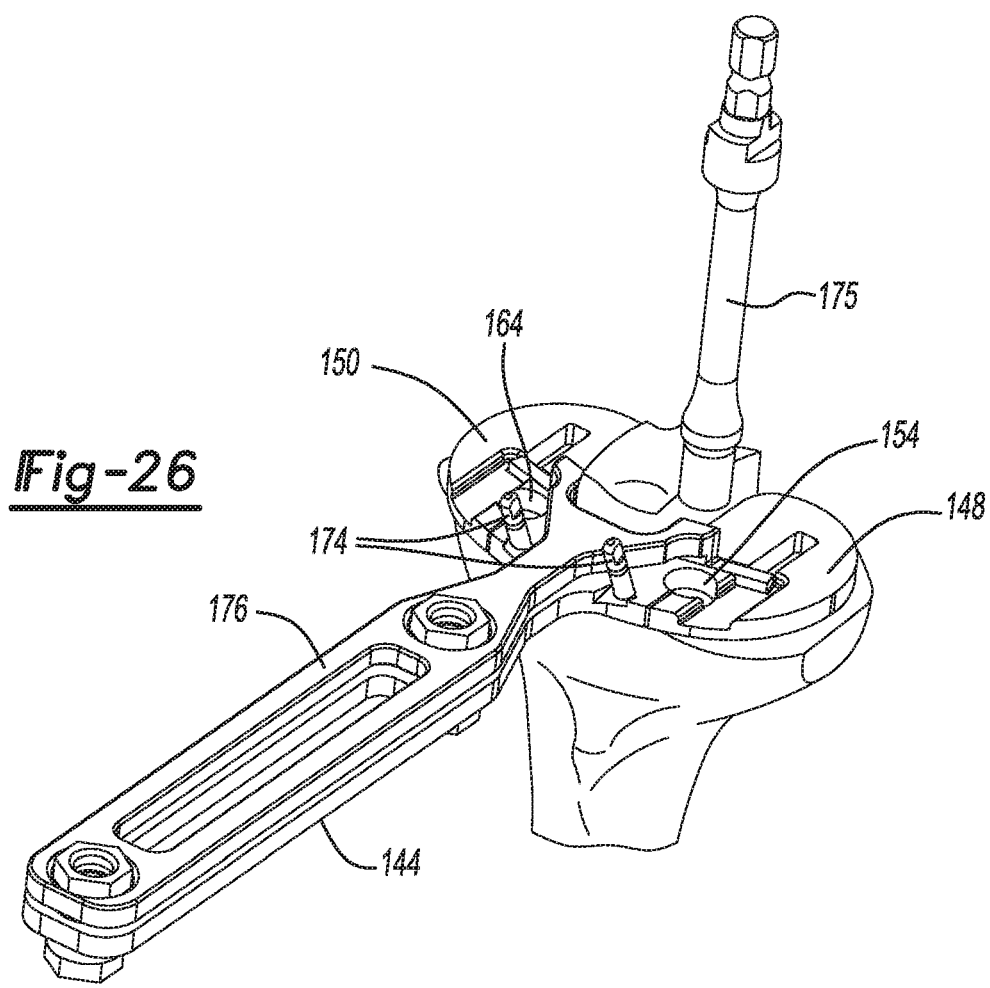
FIG. 26 is an anterior perspective view of the proximal tibia and shown with the tibial template placed thereon and shown with a drill aligned for receipt by a medial anterior grill guide on the tibial template.
Figure 27:
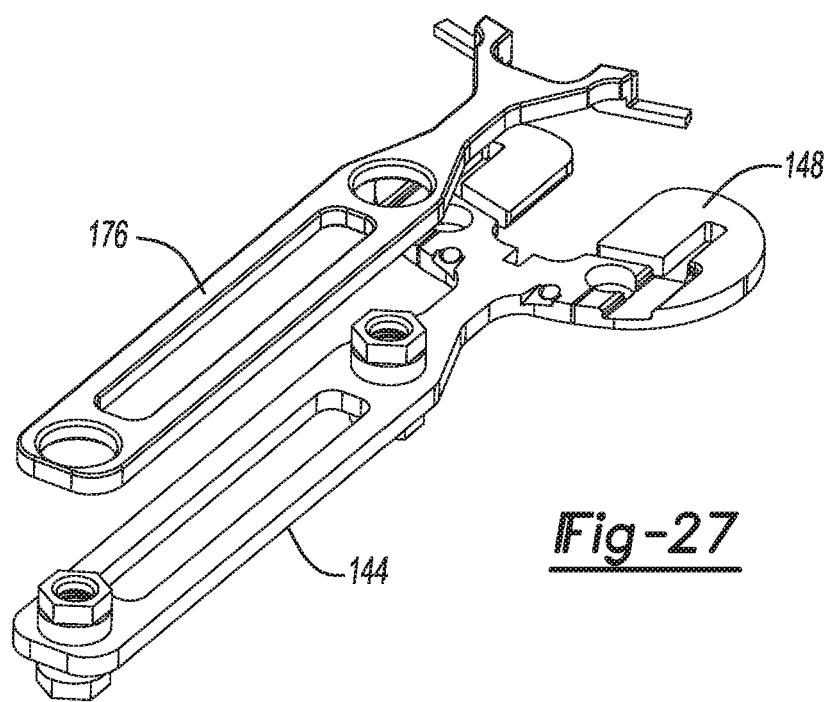
FIG. 27 is an exploded front perspective view of a tibial mask and tibial template.

Tibial preparation for an intact and functional ACL will now be described. With the tibial template 144 in proper position (FIG. 26), such as by way of pins 174, a drill 175 can be used to prepare an anterior hole while referencing the lateral anterior drill guide 154. A tibial mask 176 may be coupled to the tibial template 144. In one example, a ⅛ inch drill 175 may be used (FIG. 26). Next, another anterior hole can be drilled with the drill 175 while referencing the medial anterior drill guide 164.

Figure 28:
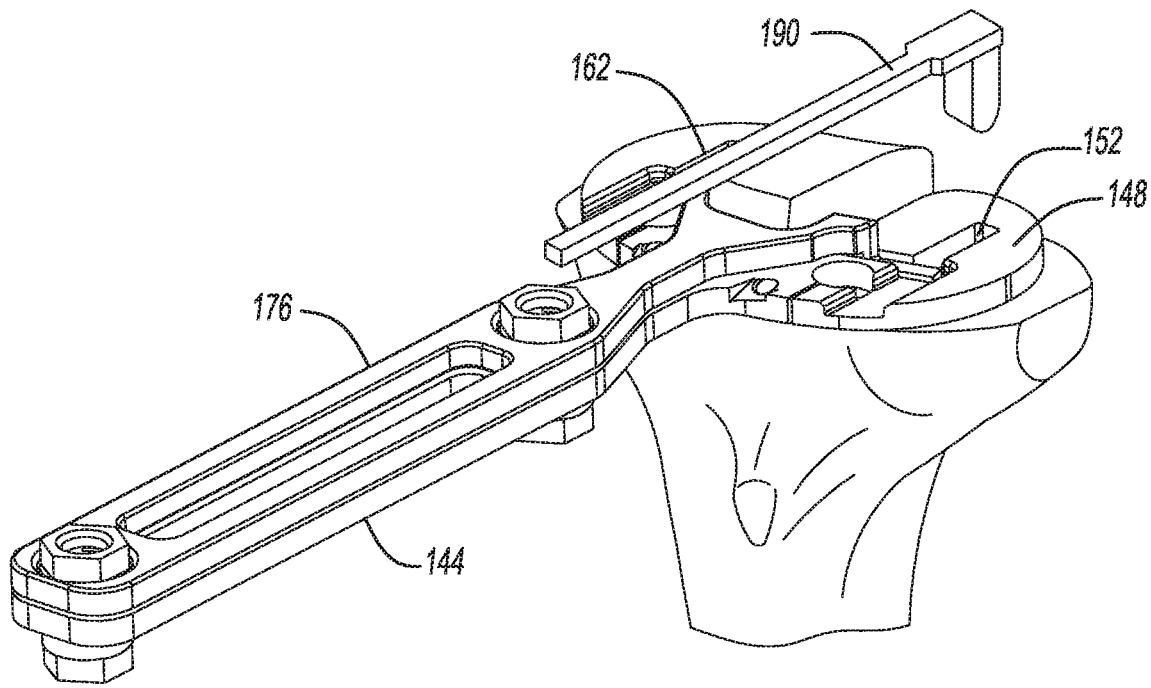
FIG. 28 is an anterior perspective view of the proximal tibia and shown with a toothbrush keel blade aligned for receipt into a medial passage provided in the tibial template.
Figure 29:
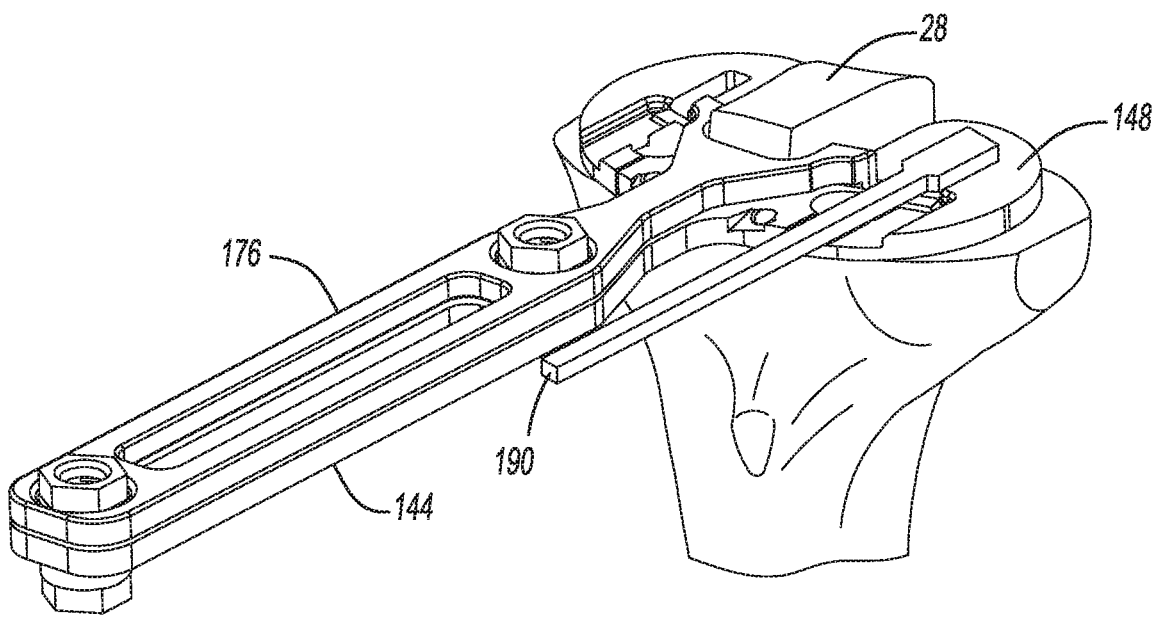
FIG. 29 is an anterior view of the proximal tibia of FIG. 28 and shown with the toothbrush keel blade received by the medial passage of the tibial template during formation of a medial groove in the tibia.
Figure 33:
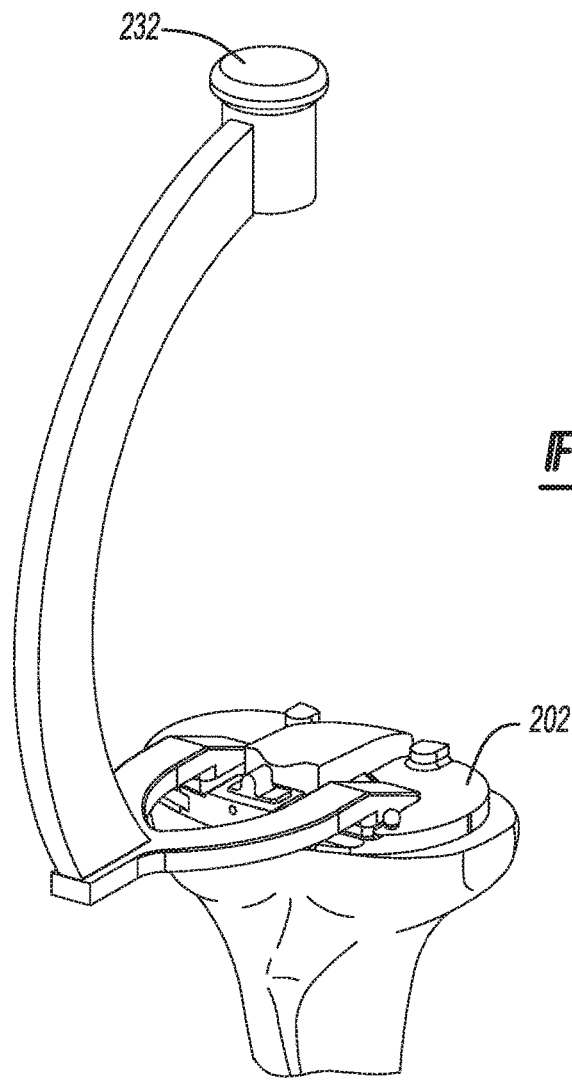
FIG. 33 is a medial perspective view of the proximal tibia and shown with a tibia bearing trial handle and tibial impactor coupled to the tibial tray trial.
Figure 34:
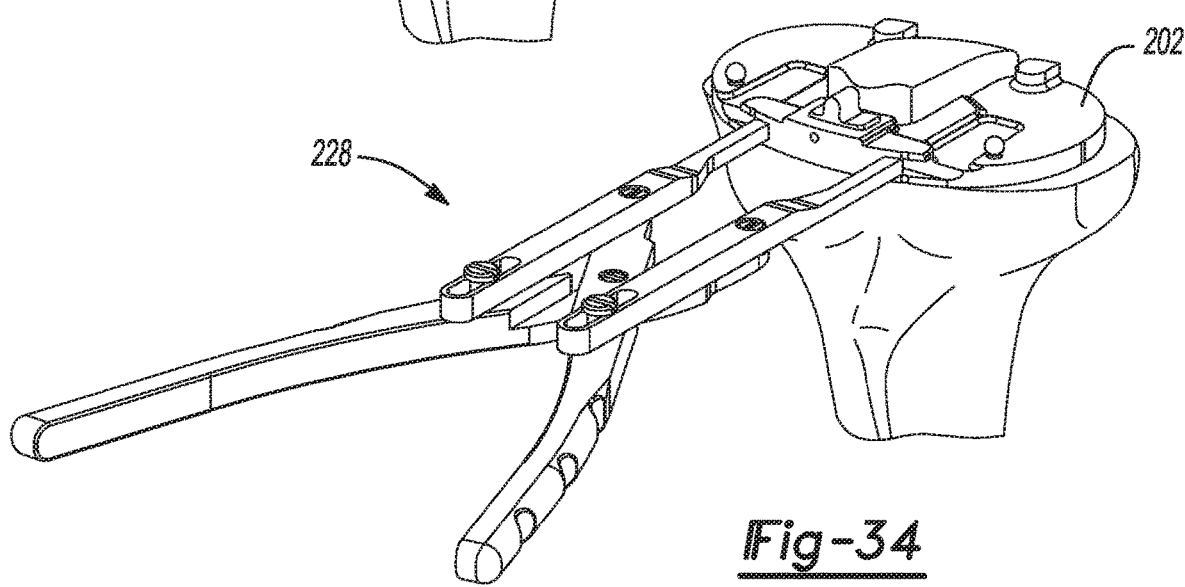
FIG. 34 is an anterior perspective view of the proximal tibia of FIG. 33 and bearing trial handle tool.
Figure 35:
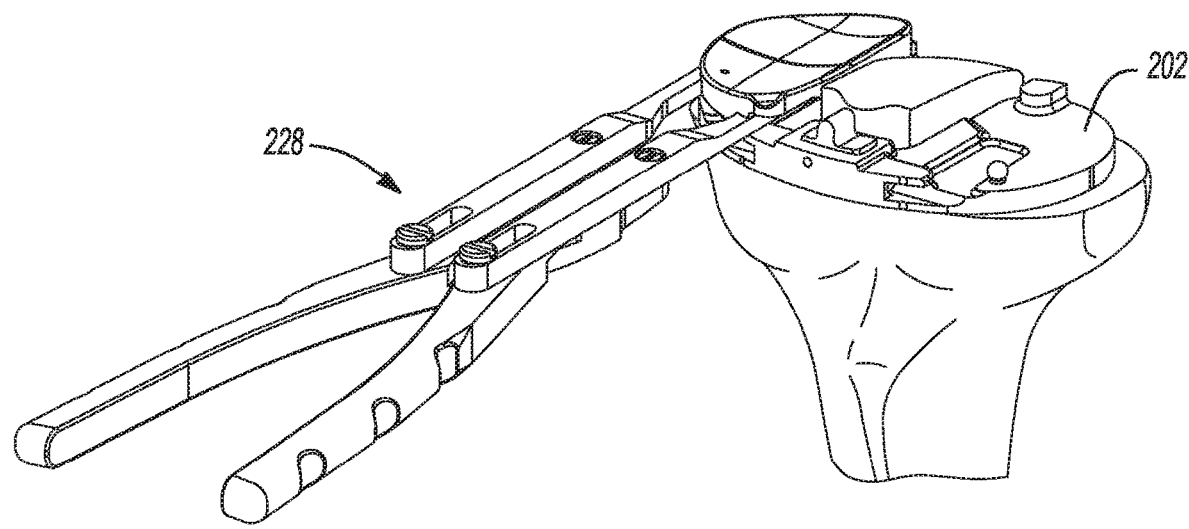
FIG. 35 is an anterior perspective view of the proximal tibia of FIG. 34 shown with the bearing trial handle tool positioning a bearing onto the tibial tray.
Figure 36:
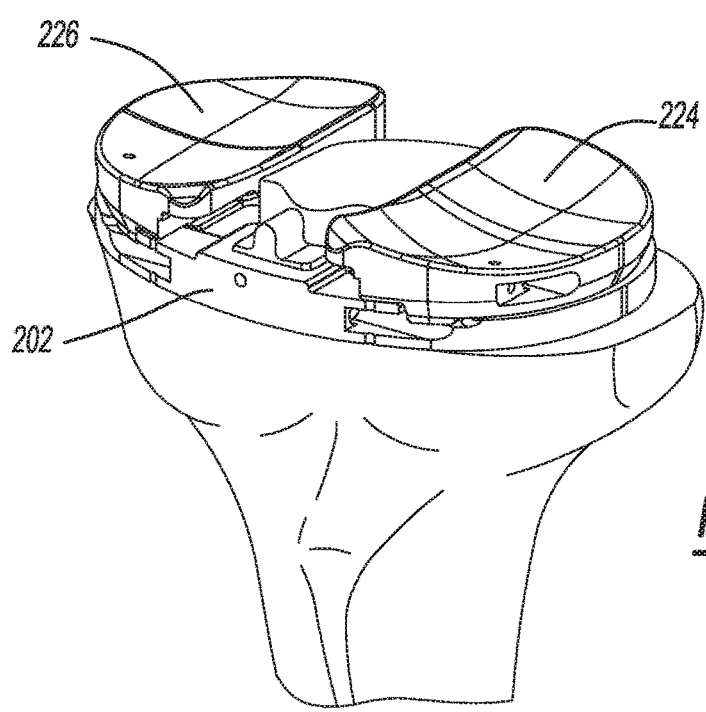
FIG. 36 is a front perspective view of the proximal tibial of FIG. 35 shown with a medial and lateral bearing coupled to the tibial tray.
Figure 37:
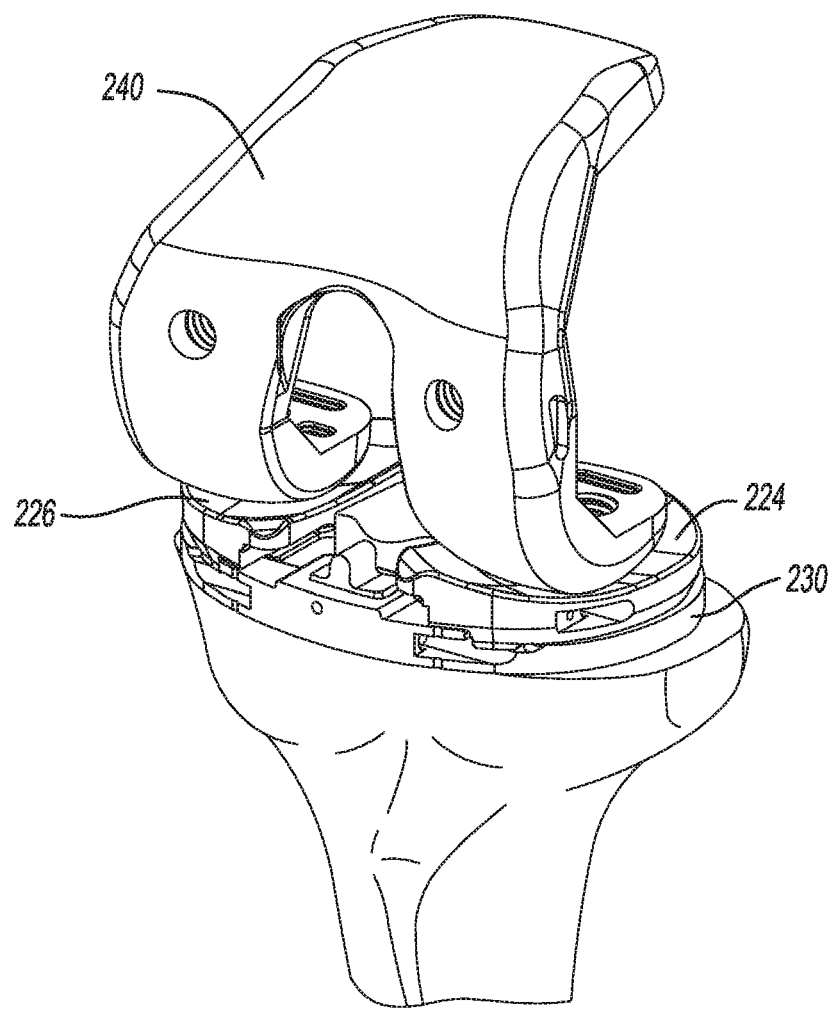
FIG. 37 is a front perspective view of the tibial tray of FIG. 36 shown with a femoral trial used to check range of motion.

With the tibial template 144 secured in place, a toothbrush keel blade 190 can be used to prepare both the medial and lateral tibia for the keeled base plate. Specifically, the toothbrush keel blade 190 can be inserted through the lateral passage 152 and the medial passage 162 (FIGS. 28 and 29). While the tibia T is being prepared, the tibial trial assembly 200 (FIGS. 30 and 31) can be prepared. The tibial trial assembly 200 can include a tibial tray trial 202 and tibial tray trial insert 204. Once tibial preparation is complete, the tibial template 144 can be removed from the proximal tibia. The tibial tray trial 202 can have multiple versions that provide various dimensions. Similarly, the tibial tray trial insert 204 can also provide various dimensions suitable for the needs of a particular patient. Of note, the tibial tray trial insert 204 includes pegs 210 and keels 213. The pegs 210 have a spacing that corresponds to the passages made earlier with the drill 175. Similarly, the keels 213 have dimensions suitable for insertion into the grooves prepared with the toothbrush keel blade 190. As illustrated in FIG. 33, a tibial tray trial 202 is shown being impacted onto the tibia T using a tibial impactor 232. As illustrated in FIGS. 34-36, a lateral tibial bearing trial 224 and a medial tibial bearing trial 226 can be coupled to the tibial tray trial 202 using a bearing trial handle tool 228 and trialed. Also, the tibial tray trial 202 can be positioned with the bearing trial handle tool 228 (FIG. 34). As shown in FIG. 37, a femoral trial 240 can be used to verify range of motion.

Figure 38A:
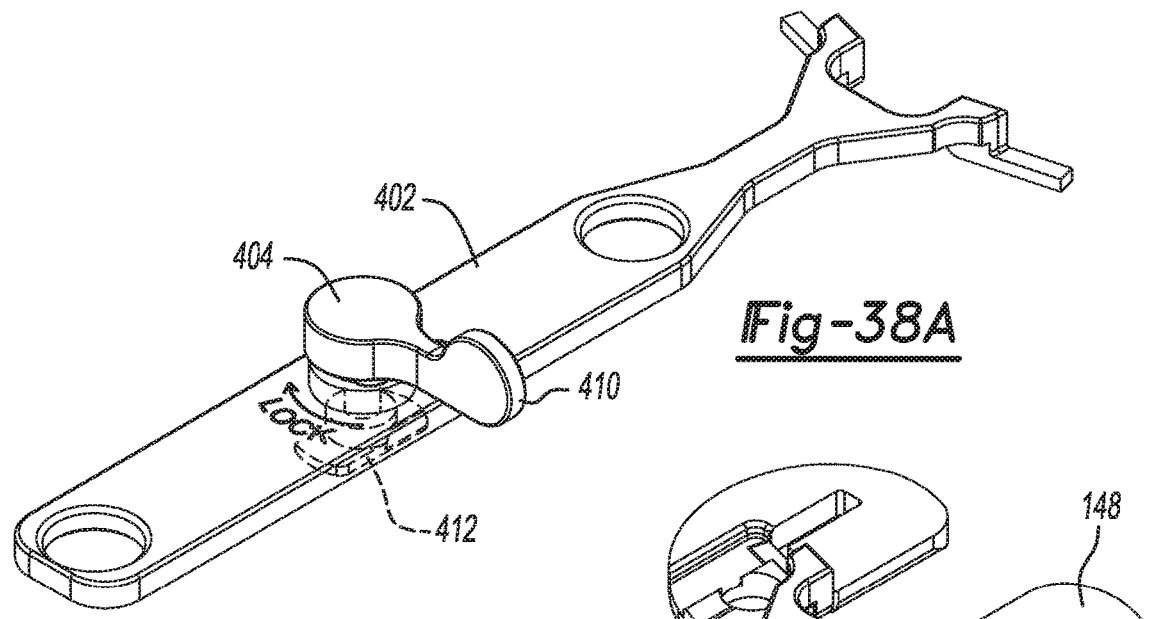
FIG. 38A is a front perspective view of a mask having a locking feature according to other features of the present disclosure.
Figure 38B:
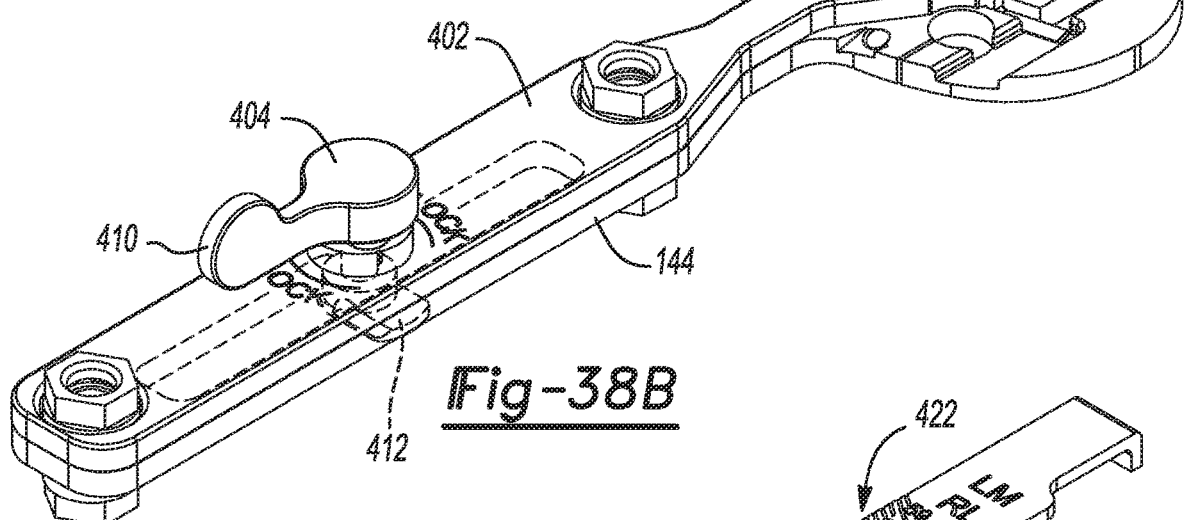
FIG. 38B illustrates the mask of FIG. 38A shown coupled to a tibial template according to one example of the present disclosure.

With reference now to FIGS. 38A-55, instruments configured to prepare the proximal tibia according to additional features will be described. FIG. 38A illustrates a mask 402. The mask 402 includes a locking feature 404 having an actuating lever 410 and a catch 412. The actuating lever 410 can be rotated from an unlocked position (FIG. 38A) to a locked position (FIG. 38B) to lock the mask 402 to the tibial template 144. In one configuration, the catch 412 can be advanced through a slot 414 defined on the tibial template 144. Rotation of the actuating lever 410 (from the unlocked position shown in FIG. 38A) can cause the catch 412 to locate under an arm of the tibial template 144 and lock the mask 402 to the tibial template 144 (FIG. 38B).

Figure 39:
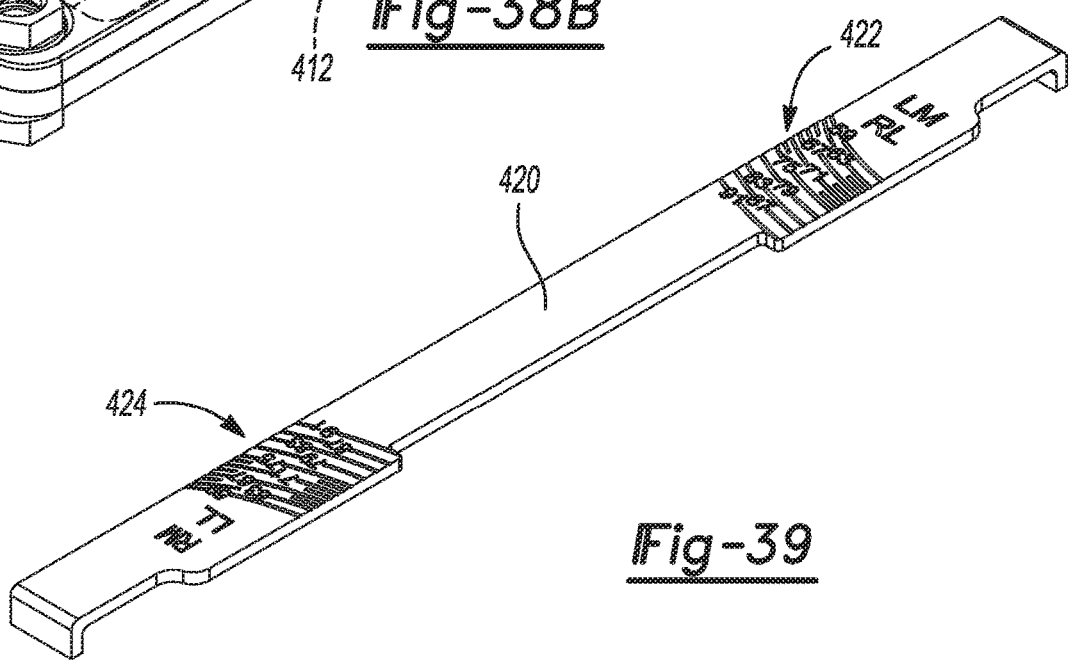
FIG. 39 is a front perspective view of a tibial sizer according to one example of the present disclosure.

FIG. 39 illustrates a tibial sizer 420. The tibial sizer 420 can be used to size a tibia in the anterior/posterior direction (see also FIG. 22). The tibial sizer 420 is formed of flat or planar material for ease of positioning. The tibial sizer includes first indicia 422 and second indicia 424. The first indicia 422 can correspond to left medial and right lateral measurements. The second indicia 424 can correspond to right medial and left lateral measurements.

Figure 40:
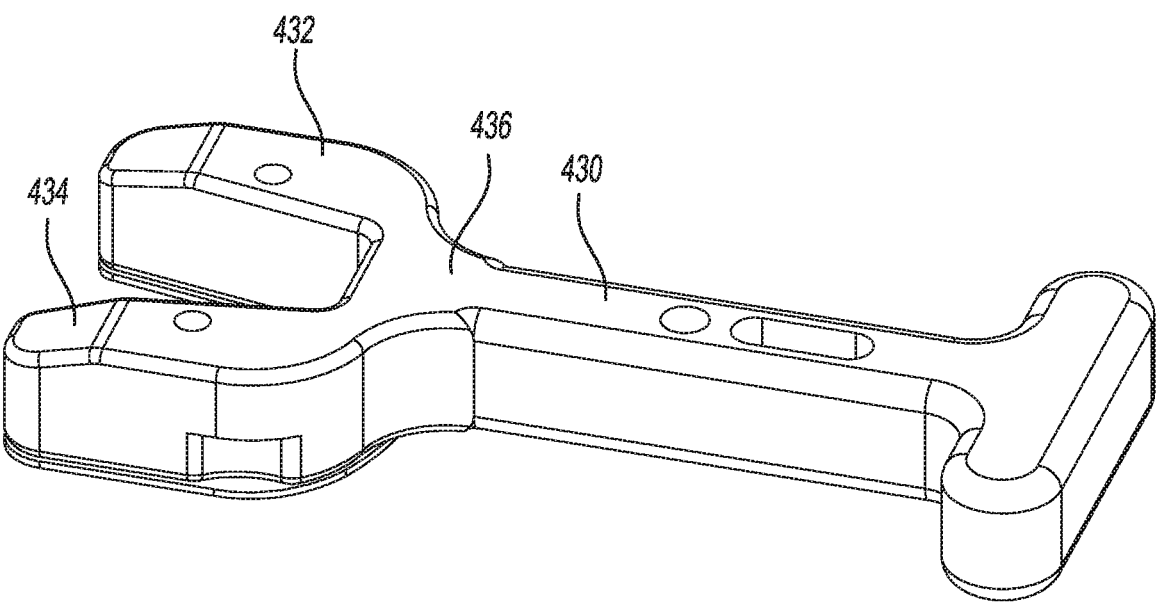
FIG. 40 is a front perspective view of a spacer block constructed in accordance with one example of the present teachings.
Figure 41:
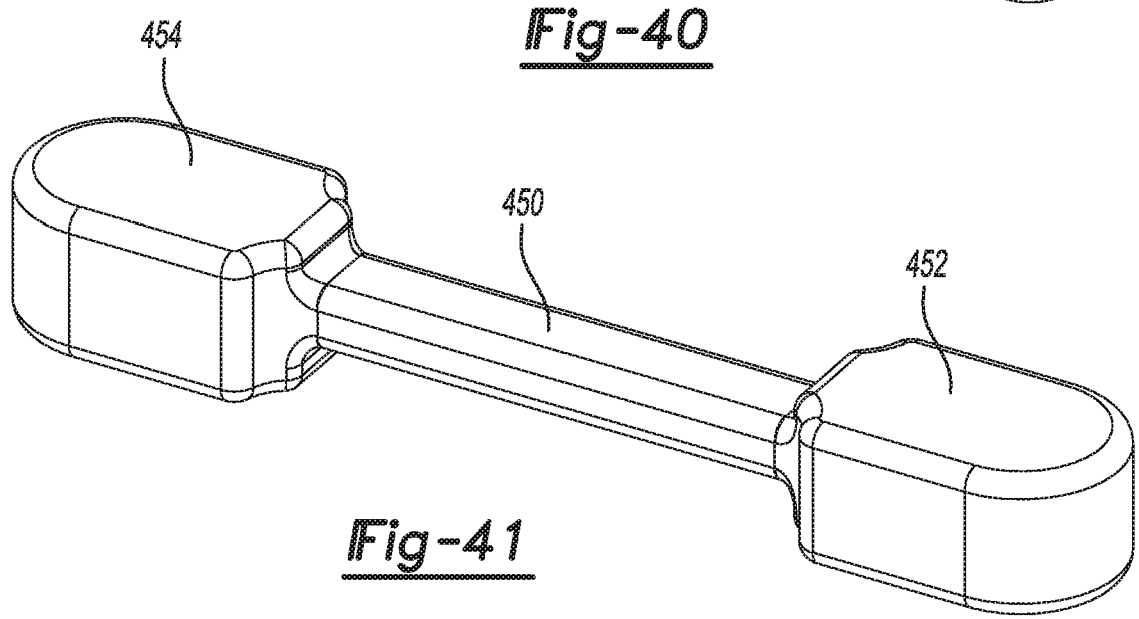
FIG. 41 is a front perspective view of another spacer block constructed in accordance to another example of the present teachings.

FIG. 40 illustrates a spacer block 430. The spacer block 430 includes fingers 432 and 434 extending from a central portion 436. The fingers 432 and 434 can diverge from the central portion 436 such that they are open to inhibit impingement on the ACL island 28. In one example, the spacer block 430 is formed of plastic. The fingers 432 and 434 can be 9 mm thick. Other thicknesses are contemplated. A spacer block 450 is shown in FIG. 41. The spacer block 450 can include a first spacer block portion 452 and a second spacer block portion 454. The first spacer block portion 452 can be 9 mm. The second spacer block portion 454 can be 10 mm. The spacer block 450 can be used to verify the medial and lateral side gaps in extension.

Figure 42:
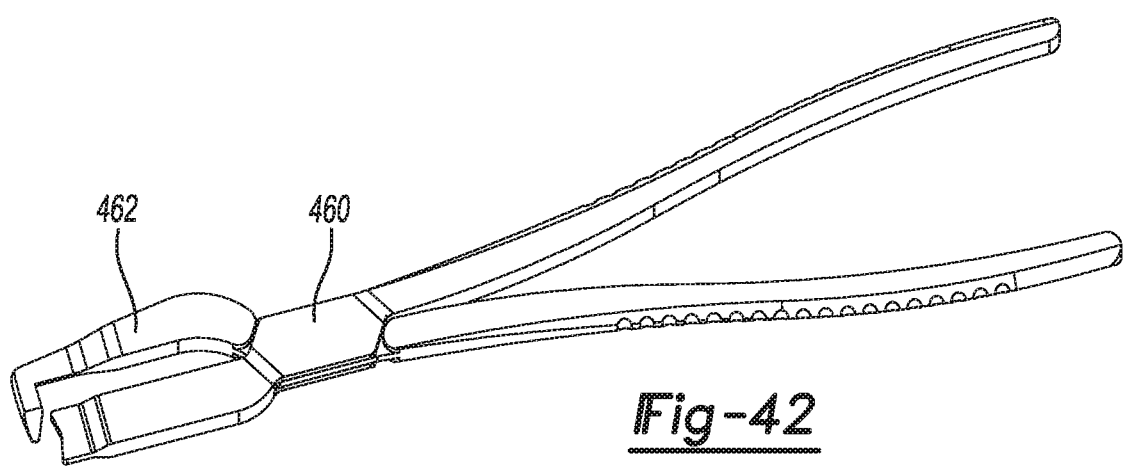
FIG. 42 is a front perspective view of a presetter tool constructed in accordance to one example of the present disclosure.
Figure 43:
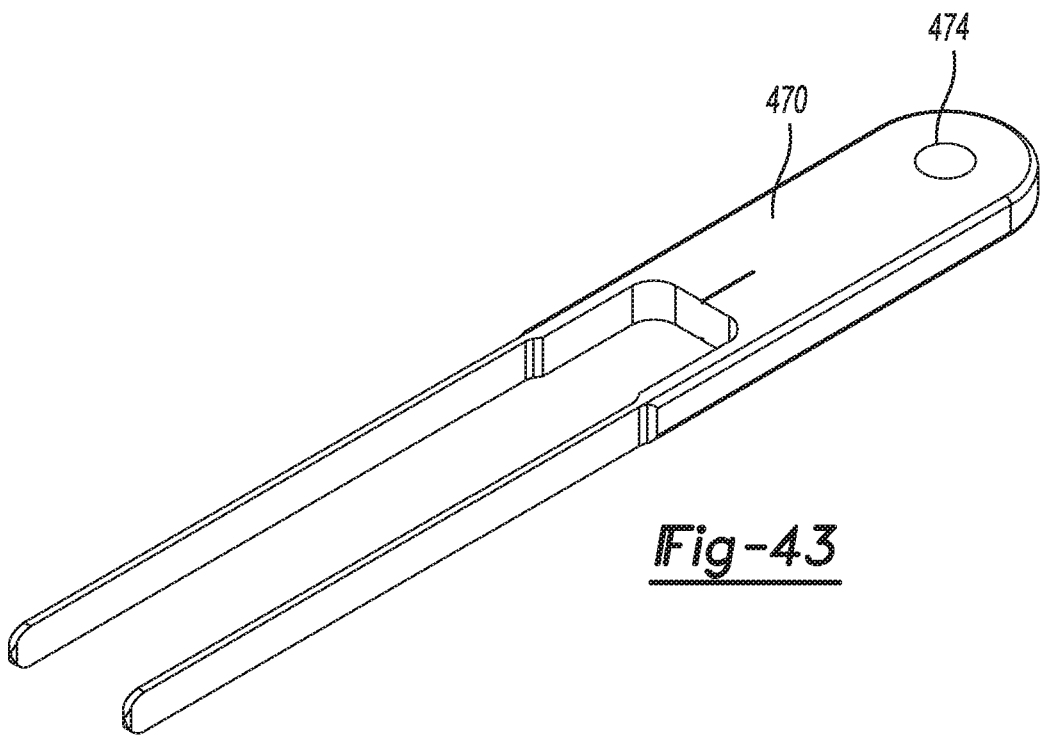
FIG. 43 is a front perspective view of an alignment guide constructed in accordance to one example of the present disclosure.

FIG. 42 illustrates a presetter tool 460. The presetter tool 460 can be used to lock tibial bearings onto a tibial tray. The presetter tool 460 comprises an arm 462 having a thin thickness that reduces potential impingement with soft tissue. FIG. 43 illustrates an alignment guide 470. The alignment guide 470 can be used to aid in the positioning of the vertical cut guide 72 (FIG. 10). The alignment guide 470 defines an aperture 474 for receipt of an alignment rod.

Figure 44:
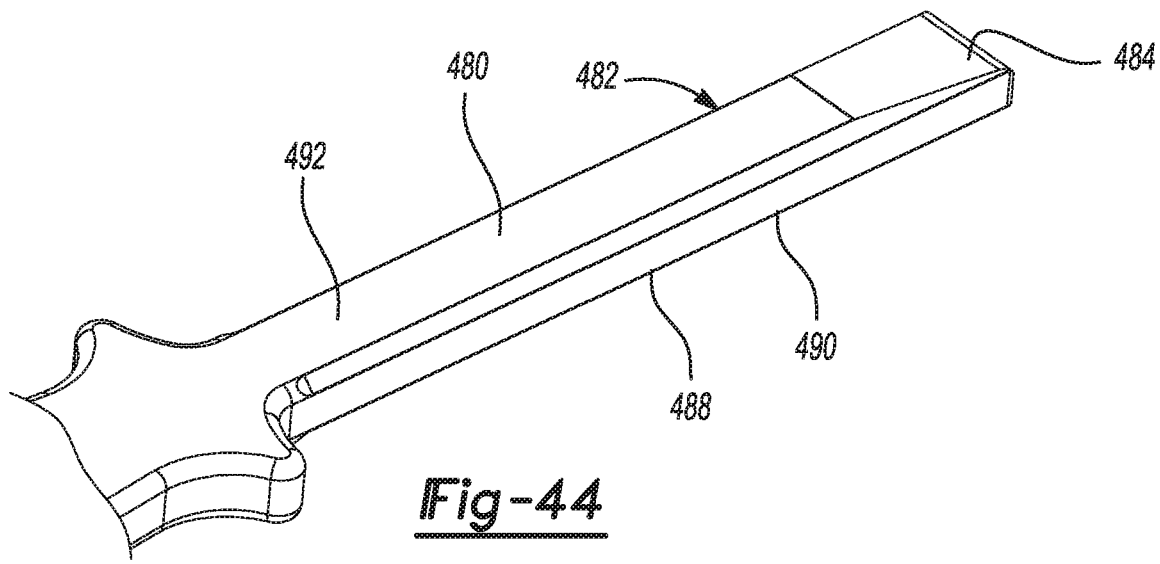
FIG. 44 is a front perspective view of a rasp constructed in accordance to one example of the present disclosure.

FIG. 44 illustrates a rasp 480. The rasp 480 includes a distal portion 482 that acts as a lead in surface that has no teeth. Such a configuration assists in avoiding the femoral condyle. The distal portion 482 has a square distal end 484 that can enable rasping of a posterior bony island. The rasp 480 can have coarse rasp teeth on sides 488 and a bottom surface 490. An upper surface 492 can have fine rasp teeth.

Figure 45A:
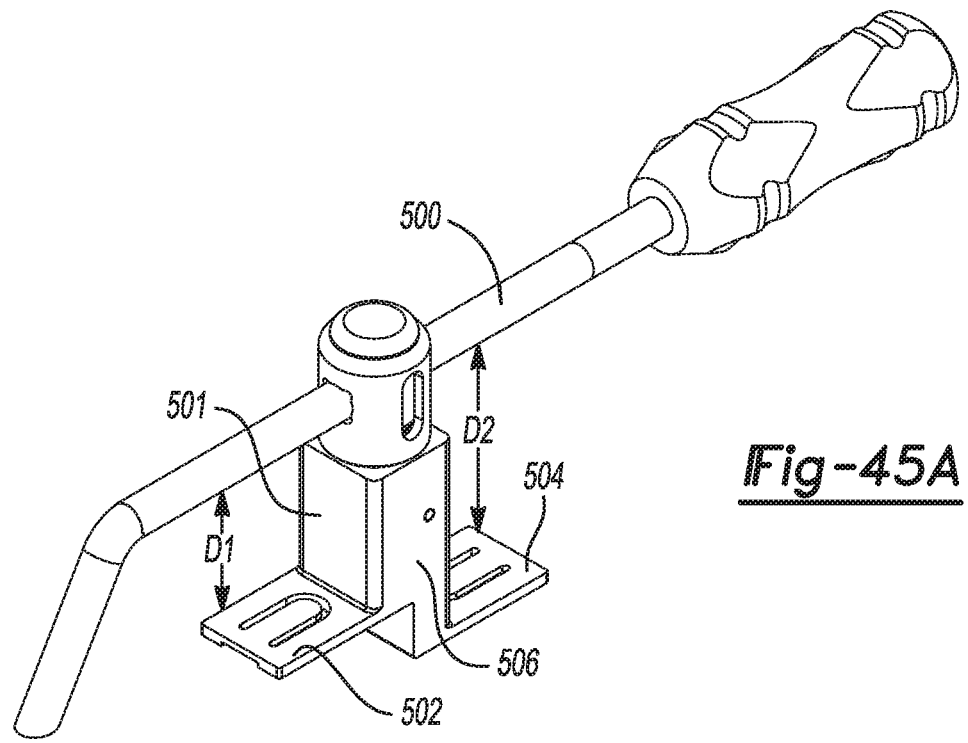
FIG. 45A is a front perspective view of a stylus constructed in accordance to one example of the present disclosure.
Figure 45B:
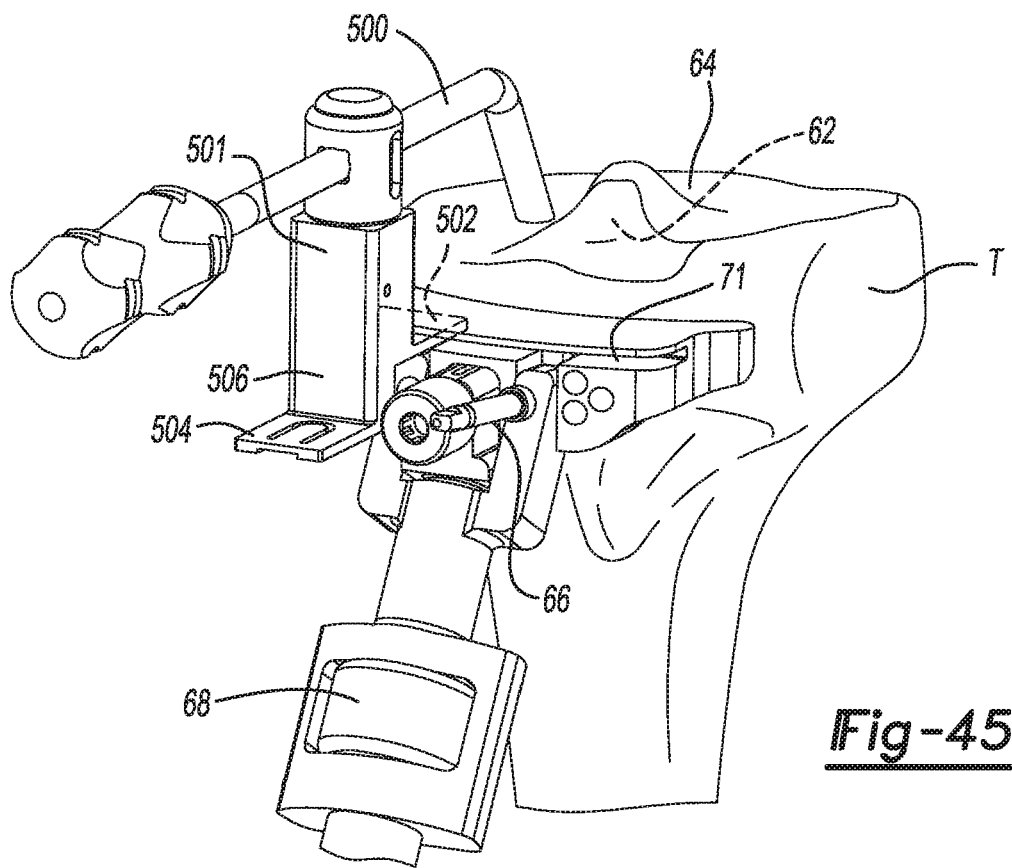
FIG. 45B is a front perspective view of the stylus of FIG. 45A shown with a first attachment portion received by the slot of the tibial resection block.
Figure 45C:
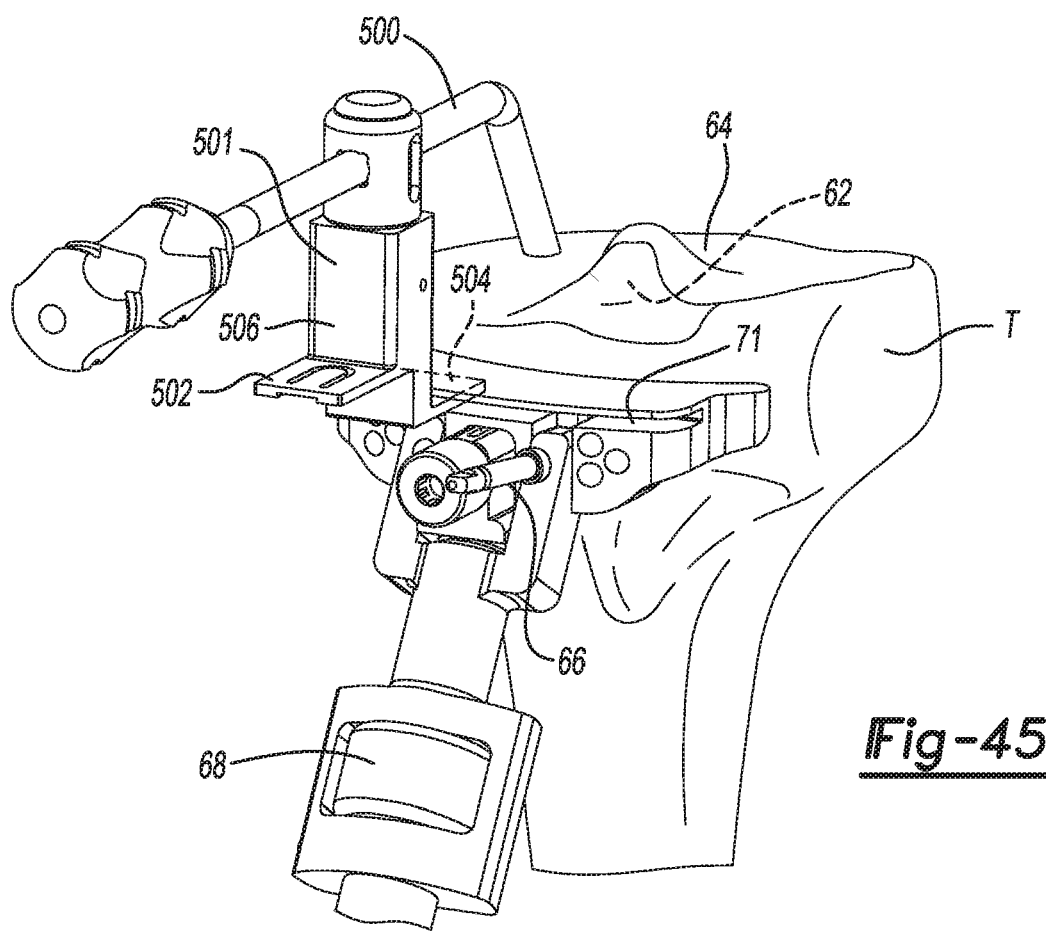
FIG. 45C is a front perspective view of the stylus of FIG. 45A shown with a second attachment portion received by the slot of the tibial resection block.

A stylus 500 constructed in accordance to one example of the present disclosure is shown in FIGS. 45A-45C. The stylus 500 can cooperate with a stylus mounting structure 501. The stylus mounting structure 501 can have a first block attachment feature 502 and a second block attachment feature 504 that oppositely extend from an attachment body 506. The first block attachment feature 502 can extend a distance D1 from the stylus 500. The second block attachment feature 504 can extend a distance D2 from the stylus 500. The distance D2 is greater than the distance D1. The first and second block attachment features 502 and 504 can both comprise a lateral projection dimensioned for receipt into the slot 71. The surgeon can select the first or second block attachment feature 502 or 504 for mating with the slot 71 (FIG. 8) depending on the more suitable distance D1 or D2 needed. As can be appreciated, the stylus 500 can be rotated 180 degrees relative to the stylus mounting structure 501 when the second block attachment feature 504 is received by the slot 71 (FIG. 8). FIG. 45B illustrates the first block attachment feature 502 mated with the slot 71. FIG. 45C illustrates the second block attachment feature 504 mated with the slot 71.

Figure 46:
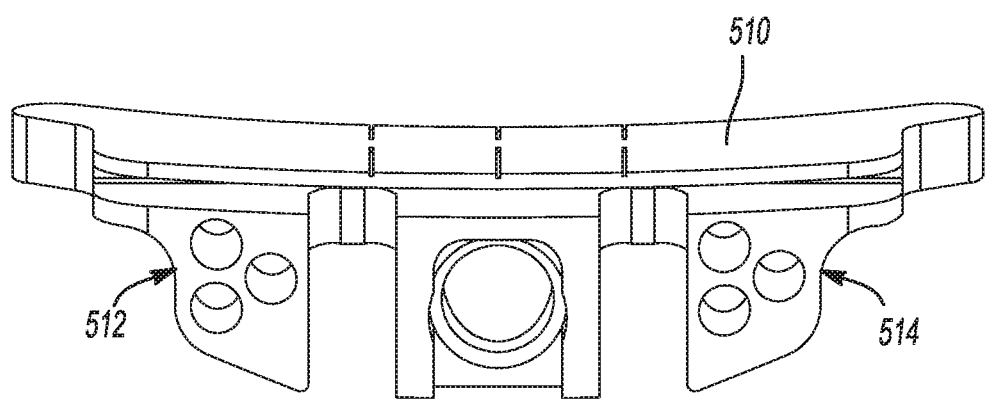
FIG. 46 is a front view of a tibial resection cut block constructed in accordance to one example of the present disclosure.
Figure 47:
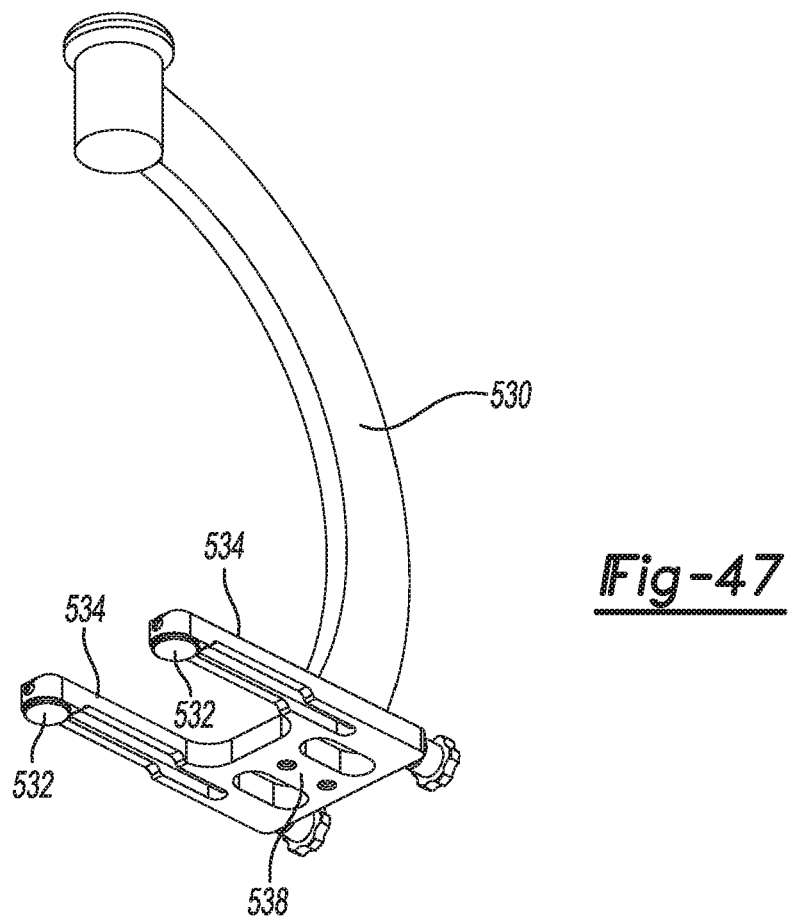
FIG. 47 is a front perspective view of an impactor constructed in accordance to one example of the present disclosure.

FIG. 46 illustrates a tibial resection cut block 510. The tibial resection cut block 510 has ends 512 and 514 that sweep inwardly to present a low profile as compared to the tibial resection cut block 70 (FIG. 8). The tibial resection cut block 510 provides a seven degree posterior slope cut inclination. FIG. 47 illustrates an impactor 530. The impactor 530 has a tray engaging portion 532 having legs 534. The legs 534 have plastic engaging pads 538 incorporated thereon.

Figure 48A:
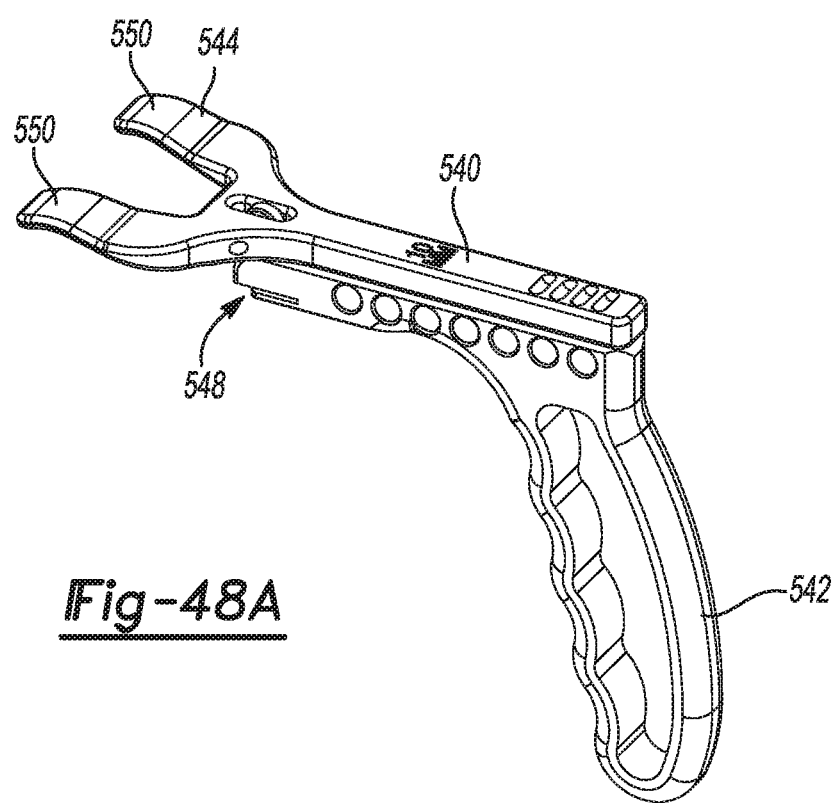
FIG. 48A is a front perspective view of a tibial resection level guide constructed in accordance to one example of the present disclosure.
Figure 48B:
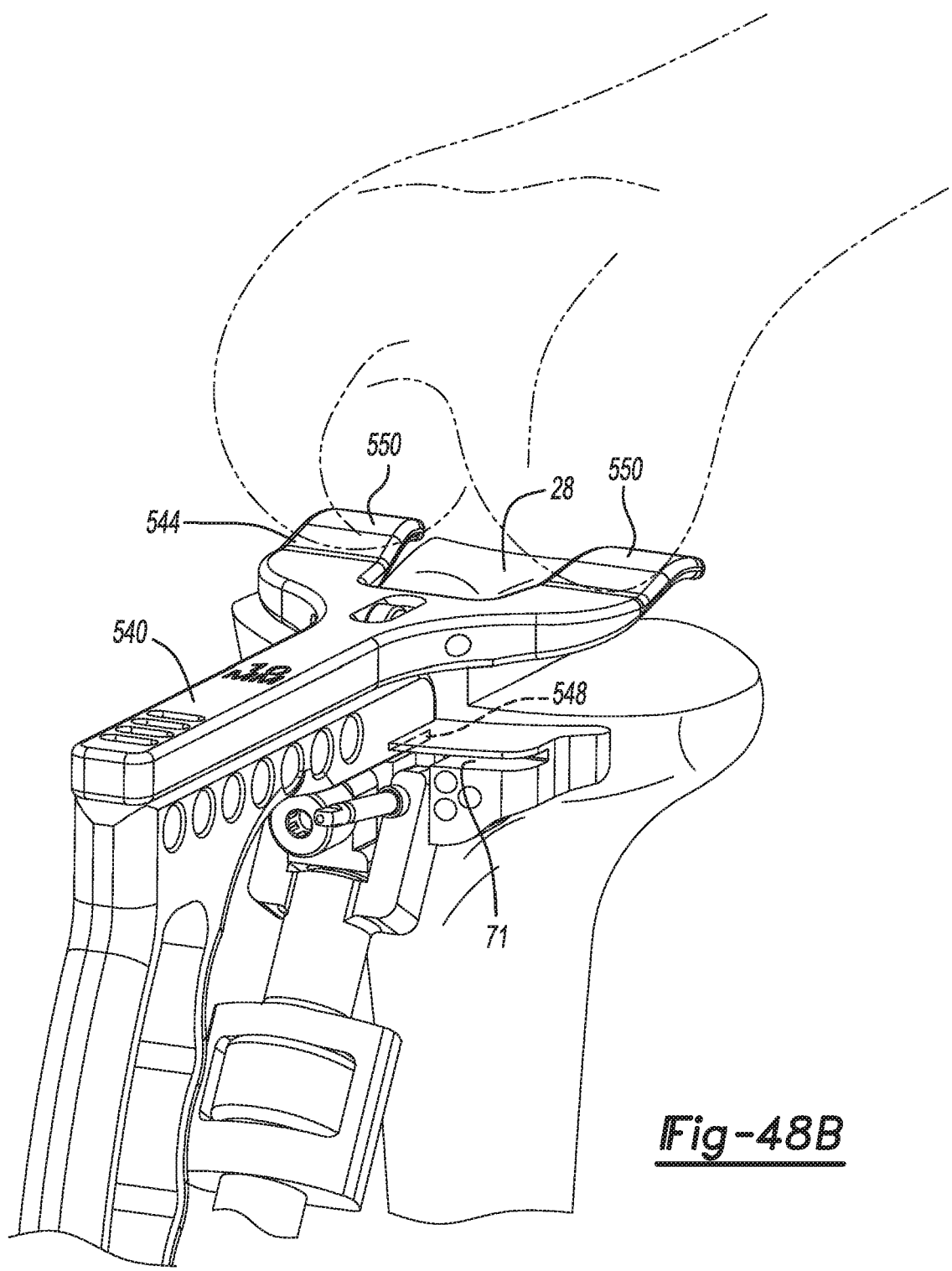
FIG. 48B is a front perspective view of the tibial resection level guide of FIG. 48A shown mated with the slot of the tibial resection guide and having an engaging end engaged to distal femoral resection surface.

FIGS. 48A and 48B. Illustrates a tibial resection level guide 540. The tibial resection level guide 540 can include a handle end 542 and an engaging end 544. The tibial resection level guide 540 can be used to assist in determining gap tension and depth of resection. In this regard, the engaging end 544 can be inserted around the ACL island 20 to help achieve an appropriate extension/flexion space. The tibial resection level guide 540 can have an attachment 548 that can be used to attach onto the horizontal slot of the tibial cutting block (see for example slot 71 of tibial cutting block 70, FIG. 8). The engaging end 544 can include paddles 550 that are configured to engage distal femoral resection surface. In one configuration, the tibial resection level guide 540 can space tibial cutting block 19 mm from the distal cut.

Figure 49:
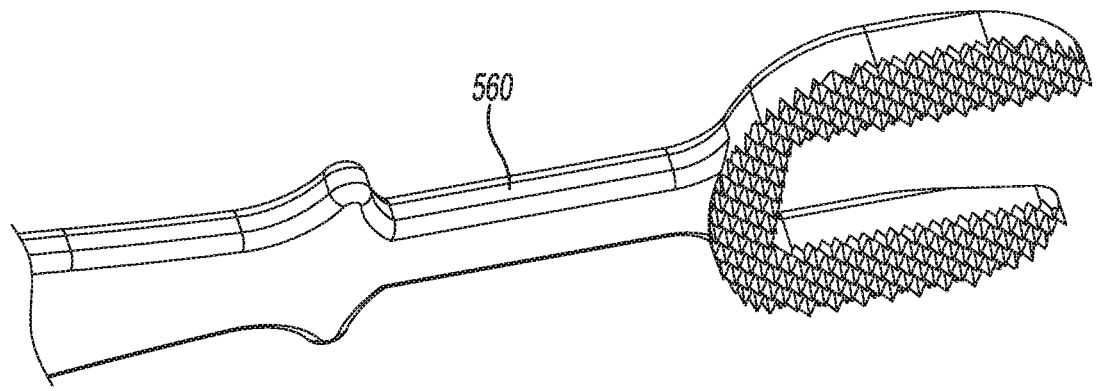
FIG. 49 is a front perspective view of a double rasp tool constructed in accordance to one example of the present disclosure.
Figure 50:
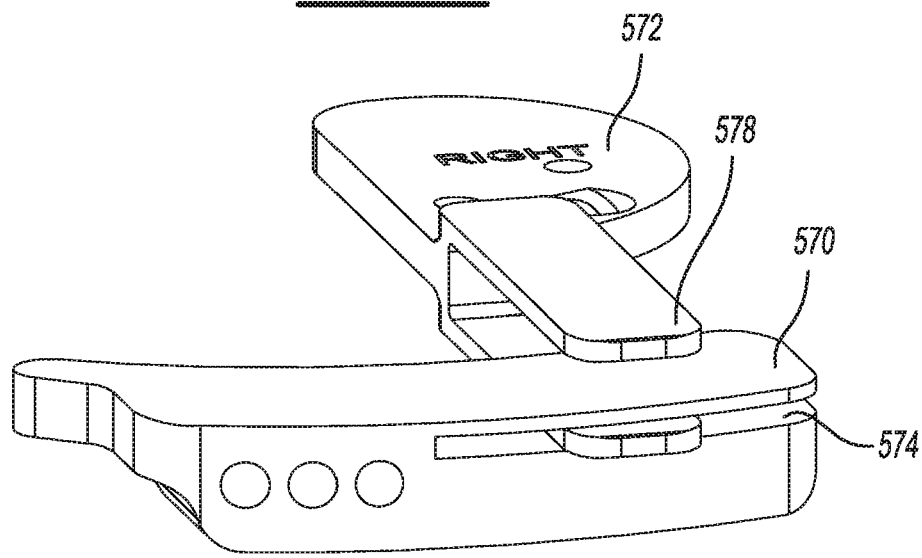
FIG. 50 is a front perspective view of a tibial resection block constructed in accordance to one example of the present disclosure.

FIG. 49 illustrates a double rasp tool 560. The double rasp tool 560 can be used to rasp the medial and lateral side of the tibia concurrently. FIG. 50 illustrates a tibial resection block 570 that cooperates with a medial plate 572. The tibial resection block 570 defines a slot 574. The medial plate 572 includes a fork 578. In one method of use, if a surgeon has made a medial cut but has yet to make a lateral cut, the medial plate 572 can be laid onto the medial resection surface. The block 570 can be located relative to the medial plate 572 and be pinned to the tibia. In this regard, the block 570 may be slid medial/lateral while the fork 578 is guided along slot 574. Lateral resection can then be prepared referencing the medial resection. By directly referencing the already prepared medial cut, the lateral cut can be made more accurately. Because the fork 578 locates relative to the slot 574, the block 570 can be rotated against the tibia but the cutting plane cannot be changed. Explained further, the cutting plane realized by the already prepared medial cut will be matched with the lateral cut.

Figure 51:
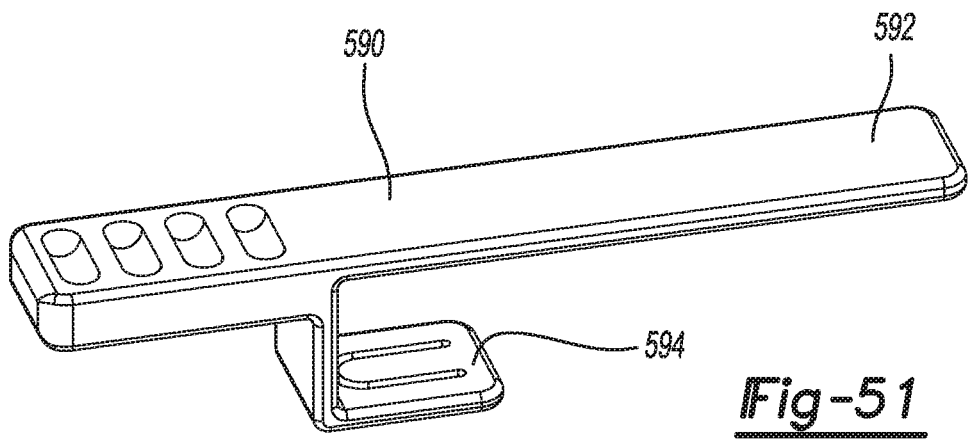
FIG. 51 is a front perspective view of an indicator tool constructed in accordance to one example of the present disclosure.

FIG. 51 illustrates an indicator tool 590. The indicator tool 590 can include an arm 592 and a finger 594. The finger 594 can locate into the slot of the tibial cutting block (see slot 71, FIG. 8). The arm 592 can be positioned to lie above the uncut tibia such that a surgeon can compare a posterior slope of the cutting block to the native posterior slope of the tibia. Before a surgeon makes any tibial cuts, the tibial cutting block (70, FIG. 8; 510, FIG. 46) can be adjusted so that the slope matches the native slope. The indicator tool 500 can be a visual aid so a surgeon can visualize the cutting block slope relative to the native slope.

FIG. 52 illustrates a tibial template tool 600. The tibial template tool 600 can have a first template end 602 and a second template end 604. The first template end 602 can have first inner fingers 610 and first outer fingers 612. The second template end 604 can have second inner fingers 616 and second outer fingers 618. The first inner fingers 610 are spaced a first distance corresponding to a first tibial island.

The second inner fingers are spaced a second distance corresponding to a second tibial island. The tibial template tool 600 can be used to accurately position the vertical cut guide 72 (FIG. 10) for creating the tibial island 20 (FIG. 4). The position and rotation of the tibial tray is determined by the position of the tibial island 20. The first outer fingers 612 can define a first outer tray footprint. The second outer fingers 618 can define a second outer tray footprint. A surgeon would benefit from knowing the ultimate position of the tray before cutting the tibia to create the tibial island 20.

Figure 7:
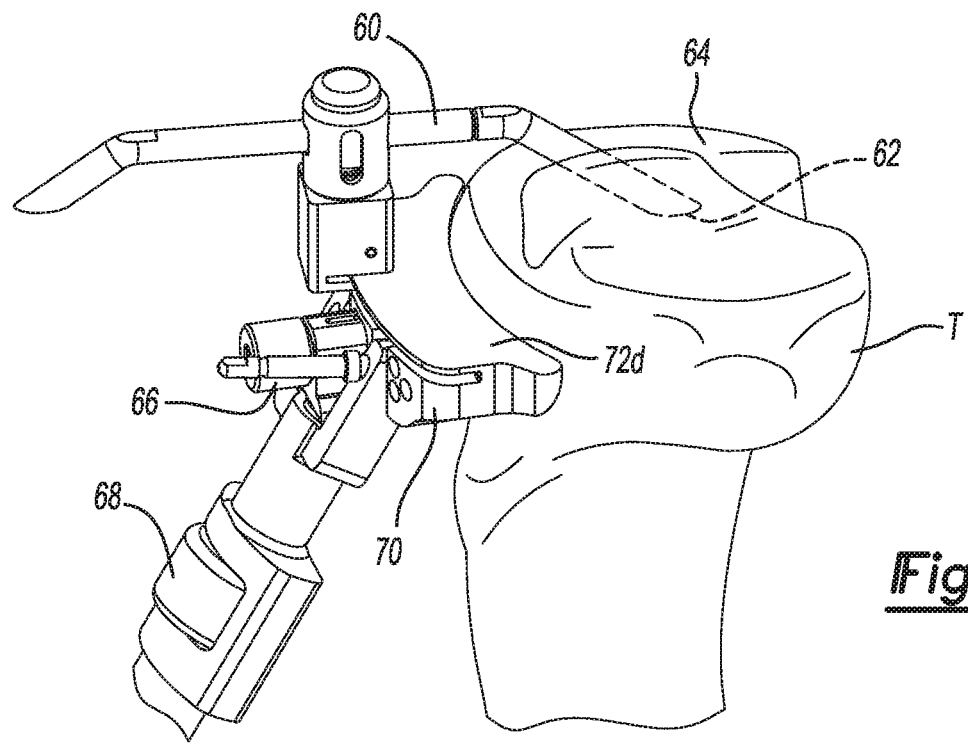
FIG. 7 is a medial perspective view of the proximal tibia of FIG. 8 shown with a terminal end of a modular stylus engaged to the lowest point of the medial tibial plateau.

The first template end 602 (or second template end 604) of the tibial template tool 600 can be laid on top of an uncut tibia T (see for example FIG. 7). The inner fingers 610 represent the bony island. The ACL will locate between the inner fingers 610. A surgeon can observe the medial/lateral coverage and tray rotation and reference either the first or second template end 602 or 604 having different sizes to represent different trays. Once the tray size and location has been determined, a marking pen can then be used to mark two lines along the inner fingers 610 to mark the preferred location of the tibial island 20. When a surgeon is ready to use the vertical cut guide 72 (FIG. 10), the vertical cut guide 72 can be positioned referencing the markings.

Figure 55:
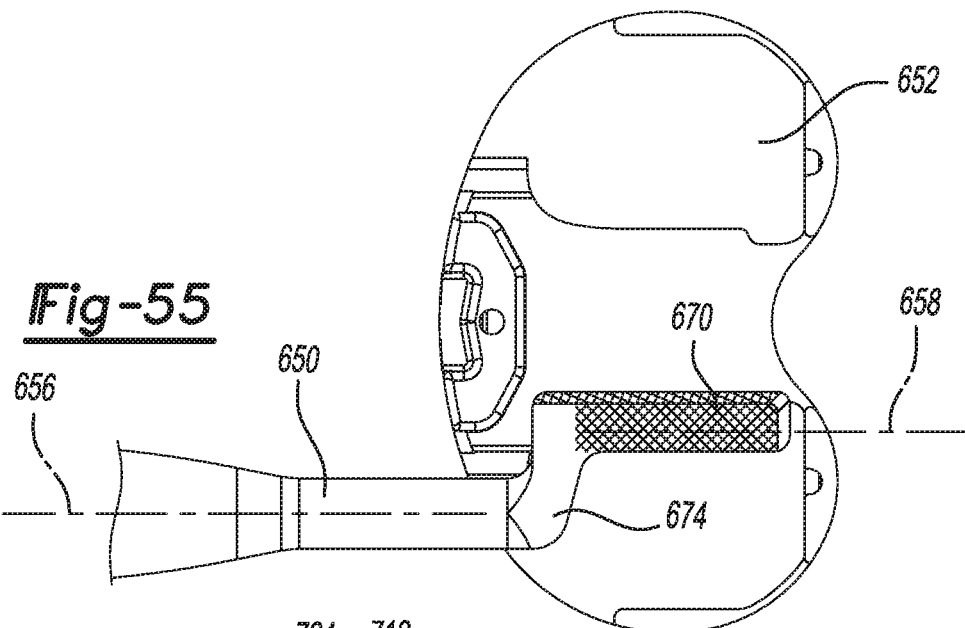
FIG. 55 is a top view of an offset rasp tool constructed in accordance to one example of the present disclosure.

FIG. 53 illustrates a holding tool 630. The holding tool 630 can be used to hold down the bearing while the locking bar is being located. FIG. 54 illustrates a tibial recutting guide 640. The tibial recutting guide 640 can be used when an initial tibial cut was not deep enough. The tibial recutting guide 640 can include a pad member 642 that can be located onto the cut tibia. The cut block 510 can be dropped 2 mm and be pinned to the tibia and the tibia can be recut. FIG. 55 illustrates an offset rasp tool 650. The offset rasp tool 650 can be used to rasp the tibial island 20 after a tray 652 has already been implanted. The offset rasp tool 650 can have a handle end 654 that extends along a first longitudinal axis 656 and a rasp end 670 that extends along a second longitudinal axis 658. The handle end 654 and the rasp end 670 are connected by an intermediate body portion 674. The first and second longitudinal axes 656 and 568 are offset allowing a surgeon to easily gain access to the tibial island 20. The rasp end 670 is dual sided allowing the surgeon to flip the tool and use it for either the medial or lateral side of the tibial island 20.

Figure 56:
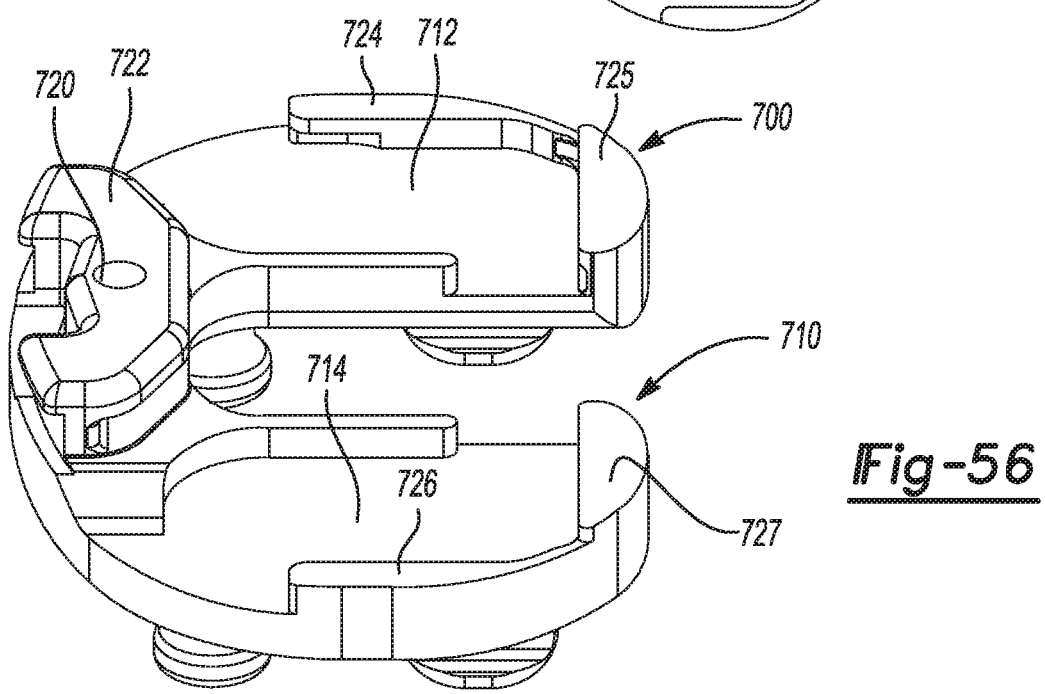
FIG. 56 is a top perspective view of an exemplary tibial tray constructed in accordance to one example of the present disclosure.

FIG. 56 illustrates a tibial tray 700 configured for implanting onto a corresponding prepared proximal tibia. The tibial tray 700, as with those described above, can be generally U-shaped and provides a slot 710 that can be configured to accommodate and provide clearance for a host ACL and/or PCL or a reconstructed ACL and/or PCL. The tray 700 can include a medial portion 712, a lateral portion 714, an anterior engagement bridge 720 and an anterior connecting portion 722. The medial portion 712 includes superiorly extending rails 724 and a posterior catch 725. The lateral portion 714 includes superiorly extending rails 726 and a posterior catch 727.

Figure 57:
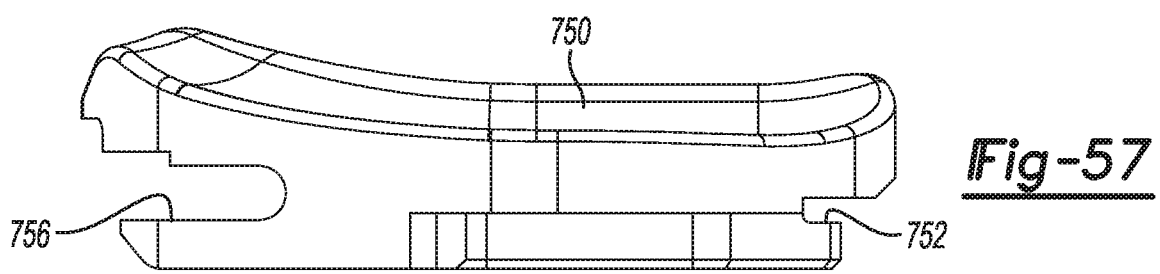
FIG. 57 is a side view of an exemplary bearing constructed in accordance to one example of the present disclosure.

FIG. 57 illustrates a lateral bearing 750. The lateral bearing 750 can selectively secure to the lateral portion 714 of the tibial tray 700. The lateral bearing 750 includes a posterior slot 752 that is configured to locate under the posterior catch 727. The lateral bearing 750 further includes an anterior slot 756. The anterior slot 756 can align relative to the anterior connecting portion 722 for receipt of a locking bar (not shown).

The foregoing description of the examples has been provided for purposes of illustration and description. It is not intended to be exhaustive or to limit the disclosure. Individual elements or features of a particular example are generally not limited to that particular example, but, where applicable, are interchangeable and can be used in a selected example, even if not specifically shown or described. The same may also be varied in many ways. Such variations are not to be regarded as a departure from the disclosure, and all such modifications are intended to be included within the scope of the disclosure.

What is claimed is:

1. A system of components for a bi-cruciate retaining procedure, the system comprising:
   a tibial tray trial having a U-shaped body portion with a lateral side and a medial side, the tibial tray trial configured to receive an island on a proximal tibia to preserve an anterior cruciate ligament of a patient;
   a tibial tray trial insert configured to be coupled to the tibial tray trial, the tibial tray trial insert having a U-shaped body portion with a lateral side and a medial side configured to rest on a resected surfaces of the proximal tibia, the tibial tray trial configured to receive the island on the proximal tibia to preserve the anterior cruciate ligament of the patient, the tibial tray trial insert including at least one of a peg and keel configured to insert into one or more prepared recesses in the proximal tibia; and
   a lateral tibial bearing trial and a medial tibial bearing trial configured to couple to the tibial tray trial, the lateral tibial bearing trial configured to couple to the lateral side of the tibial tray trial and be disposed lateral of the island when assembled and the medial tibial bearing trial configured to couple to the medial side of the tibial tray trial and be disposed medial of the island when assembled.

2. The system of claim 1, further comprising a tibial template having a U-shaped body portion with a lateral side and a medial side, the tibial template configured to leave intact the island, the template forming a lateral passage and a lateral anterior drill guide on the lateral side.

3. The system of claim 2, wherein the tibial template further includes apertures there through configured to receive at least one pin.

4. The system of claim 2, further comprising a tibial mask configured to couple to the tibial template.

5. The system of claim 2, wherein the tibial template includes one or more slots therethrough, the slots configured to receive a cutting tool that is operable to prepare a keel recess in the proximal tibia.

6. The system of claim 1, wherein both the a tibial tray trial and the a tibial tray trial insert have a plurality of versions each version defined by different dimensions.

7. The system of claim 1, further comprising:
   a tibial resection block configured to be fixed to an anterior portion of the proximal tibia, the tibial resection block defining a first slot that continuously extends in a medial-lateral direction, the first slot configured to act as a guide for performing a proximal resection of both the medial portion and the lateral portion of the proximal tibia; and
   a vertical cut guide configured to be received in and to slidably translate along the first slot of the tibial resection block in the medial-lateral direction, the vertical cut guide configured to define both a medial slot for performing a first sagittal resection of the medial portion of the proximal tibia and a lateral slot for performing a second sagittal resection of the lateral portion of the proximal tibia.

8. The system of claim 7, wherein the vertical cut guide is configured such that the medial and lateral slots are open at a proximal surface of the vertical cut guide.

9. The system of claim 7, wherein the vertical cut guide is configured such that the medial and lateral slots are each at least partially closed by a wall at a proximal surface of the vertical cut guide.

10. The system of claim 7, wherein the medial and lateral slots terminate at partial bores that are configured to receive pins therein.

11. The system of claim 10, wherein the pins are configured to inhibit undercutting of the island during the first sagittal resection and the second sagittal resection.

12. The system of claim 10, further comprising an alignment guide with elongated arms that are configured to be slidably located in the medial and lateral slots, the alignment guide configured to aid in positioning of the vertical cut guide relative to the medial portion and the lateral portion of the proximal tibia.

13. The system of claim 10, further comprising a tibial resection guide configured to couple to the vertical cut guide and rotate relative thereto, the tibial resection guide having a stylus configured to engage a lowest point of a medial tibial plateau.

14. The system of claim 10, further comprising a locking arm coupled to the cut guide at a location between the medial and lateral slots, the locking arm movable between an unlocked position where the vertical cut guide is permitted to translate within the first slot and a locked position where the locking arm engages the tibial resection block and inhibits movement of the vertical cut guide relative to the tibial resection block.

15. The system of claim 10, wherein the vertical cut guide is configured to be adjustable relative to the tibial resection block and is configured with a body to space the medial and lateral slots relative one another to set a location for the first and second sagittal resections.

16. A system of components for a bi-cruciate retaining procedure, the system comprising:
a tibial tray trial having a U-shaped body portion with a lateral side and a medial side, the tibial tray trial configured to receive an island on a proximal tibia to preserve an anterior cruciate ligament of a patient;
a tibial tray trial insert configured to be coupled to the tibial tray trial, the tibial tray trial insert having a U-shaped body portion with a lateral side and a medial side configured to rest on a resected surfaces of the proximal tibia, the tibial tray trial configured to receive the island on the proximal tibia to preserve the anterior cruciate ligament of the patient, the tibial tray trial insert including at least one of a peg and keel configured to insert into one or more prepared recesses in the proximal tibia;
a lateral tibial bearing trial and a medial tibial bearing trial configured to couple to the tibial tray trial, the lateral tibial bearing trial configured to couple to the lateral side of the tibial tray trial and be disposed lateral of the island when assembled and the medial tibial bearing trial configured to couple to the medial side of the tibial tray trial and be disposed medial of the island when assembled; and
a tibial template having a U-shaped body portion with a lateral side and a medial side, the tibial template configured to leave intact the island, the template forming a lateral passage and a lateral anterior drill guide on the lateral side.

17. The system of claim 16, wherein the tibial template further includes apertures therethrough configured to receive at least one pin.

18. The system of claim 16, further comprising a tibial mask configured to couple to the tibial template.

19. The system of claim 16, wherein the tibial template includes one or more slots therethrough, the slots configured to receive a cutting tool that is operable to prepare a keel recess in the proximal tibia.

20. A system of components for a bi-cruciate retaining procedure, the system comprising:
a tibial tray trial having a U-shaped body portion with a lateral side and a medial side, the tibial tray trial configured to receive an island on a proximal tibia to preserve an anterior cruciate ligament of a patient;
a tibial tray trial insert configured to be coupled to the tibial tray trial, the tibial tray trial insert having a U-shaped body portion with a lateral side and a medial side configured to rest on a resected surfaces of the proximal tibia, the tibial tray trial configured to receive the island on the proximal tibia to preserve the anterior cruciate ligament of the patient, the tibial tray trial insert including at least one of a peg and keel configured to insert into one or more prepared recesses in the proximal tibia; and
a tibial template having a U-shaped body portion with a lateral side and a medial side, the tibial template configured to leave intact the island, the template forming a lateral passage and a lateral anterior drill guide on the lateral side.

21. The system of claim 20, wherein the tibial template includes one or more slots therethrough, the slots configured to receive a cutting tool that is operable to prepare a keel recess in the proximal tibia.

* * * * *

UNITED STATES PATENT AND TRADEMARK OFFICE
CERTIFICATE OF CORRECTION

| | | |
|---|---|---|
| PATENT NO. | : 11,771,442 B2 | |
| APPLICATION NO. | : 16/419459 | |
| DATED | : October 3, 2023 | |
| INVENTOR(S) | : Metzger et al. | |

It is certified that error appears in the above-identified patent and that said Letters Patent is hereby corrected as shown below:

On the Title Page

On page 2, in Column 2, Item (56) under "U.S. Patent Documents", Line 29, after "606/88", insert --¶2010/0305710 A1 12/2010 Metzger--

In the Claims

In Column 14, Line 41, in Claim 3, delete "there through" and insert --therethrough-- therefor In Column 14, Line 49, in Claim 6, after "the", delete "a"

In Column 14, Line 50, in Claim 6, after "the", delete "a"

Signed and Sealed this
Thirtieth Day of January, 2024

Katherine Kelly Vidal
*Director of the United States Patent and Trademark Office*